(12) United States Patent
Cockrem et al.

(10) Patent No.: US 6,926,810 B2
(45) Date of Patent: Aug. 9, 2005

(54) PROCESS FOR OBTAINING AN ORGANIC ACID FROM AN ORGANIC ACID AMMONIUM SALT, AN ORGANIC ACID AMIDE, OR AN ALKYLAMINE ORGANIC ACID COMPLEX

(75) Inventors: Michael Charles Milner Cockrem, Madison, WI (US); Istvan Kovacs, Madison, WI (US)

(73) Assignee: A. E. Staley Manufacturing Co., Decatur, IL (US)

( * ) Notice: Subject to any disclaimer, the term of this patent is extended or adjusted under 35 U.S.C. 154(b) by 714 days.

(21) Appl. No.: 09/809,243

(22) Filed: Mar. 15, 2001

(65) Prior Publication Data

US 2003/0029711 A1 Feb. 13, 2003

(51) Int. Cl.$^7$ .............................. B01D 3/10; B01D 3/14; B01D 3/36; C07C 51/46; C07C 51/48

(52) U.S. Cl. ................................ 203/63; 203/2; 203/68; 203/69; 203/70; 203/84; 203/94; 435/139; 435/140; 435/141; 435/142; 562/580; 562/589; 562/593; 562/607; 562/608; 516/DIG. 7

(58) Field of Search ........................ 203/2, 63, 68–70, 203/91–99, 84–85, 15–16, 34, 43, DIG. 11, DIG. 19; 562/580, 589, 593, 607, 608; 516/DIG. 7; 435/139–142

(56) References Cited

U.S. PATENT DOCUMENTS

| 321,925 A | | 7/1885 | Waite ........................... 203/95 |
| 2,050,234 A | * | 8/1936 | Othmer ........................ 203/16 |
| 3,419,478 A | * | 12/1968 | Izard ........................... 203/70 |

(Continued)

FOREIGN PATENT DOCUMENTS

| GB | 1 576 787 | * | 10/1980 |
| WO | WO98/24777 | | 6/1998 |
| WO | WO98/55442 | | 12/1998 |
| WO | WO99/19290 | | 4/1999 |
| WO | WO00/64850 | | 11/2000 |
| WO | 64850 | * | 11/2000 |

OTHER PUBLICATIONS

Perry, "Azeotropic Distillation"; *Chemical Engineers' Handbook, Fifth Edition*, 13:36–42, 1973.
Holten, "Lactic acid; properties and chemistry of lactic acid and derivates", pp. 20–21, p. 36–37, and p. 425, 1971.
CRC Handbook of Chemistry and Physics, pps. DI–D33, 1981–1982.

(Continued)

*Primary Examiner*—Virginia Manoharan
(74) *Attorney, Agent, or Firm*—Williams, Morgan & Amerson, P.C.

(57) ABSTRACT

Disclosed herein are methods for the recovery of an organic acid, such as a heat stable lactic acid, from a feed stream which contains at least one of an organic acid amide, an organic acid ammonium salt, or an alkylamine-organic acid complex. The feed stream is mixed with at least one azeotroping agent. The azeotroping agent is a hydrocarbon capable of forming at least one azeotrope with the organic acid that is produced by the thermal decomposition of the amide, ammonium salt, or complex in the feed stream. Preferably the azeotrope is a heteroazeotrope. The mixture of the feed stream and the azeotroping agent is heated to produce a vapor stream. The azeotrope is a component of the vapor stream. The vapor stream can be condensed to a liquid stream, and the organic acid is recovered in the liquid stream that is produced. When the azeotrope is a heteroazeotrope, the vapor stream can be condensed into a liquid stream, which can be separated into a first phase and a second phase. The first phase contains the highest concentration of organic acid and the second phase contains azeotroping agent. The organic acid can be further purified and/or concentrated from the separated first phase or from the liquid stream.

58 Claims, 3 Drawing Sheets

U.S. PATENT DOCUMENTS

| | | | | |
|---|---|---|---|---|
| 3,432,401 A | * | 3/1969 | Tcherkawsky | 203/15 |
| 3,718,545 A | * | 2/1973 | Horlenko | 203/15 |
| 4,100,189 A | | 7/1978 | Mercier | 562/607 |
| 4,191,616 A | * | 3/1980 | Baker | 203/44 |
| 4,275,234 A | | 6/1981 | Baniel et al. | 562/584 |
| 5,068,418 A | * | 11/1991 | Kulprathipanja et al. | 562/580 |
| 5,068,419 A | | 11/1991 | Kulprathipanja et al. | 562/580 |
| 5,138,074 A | | 8/1992 | Bellis et al. | 549/274 |
| 5,319,107 A | | 6/1994 | Benecke et al. | 549/274 |
| 5,510,526 A | * | 4/1996 | Baniel et al. | 562/580 |
| 5,574,180 A | | 11/1996 | McQuigg et al. | 558/147 |
| 5,641,406 A | | 6/1997 | Sarhaddar et al. | 210/656 |
| 5,780,678 A | | 7/1998 | Baniel et al. | 562/580 |
| 5,831,122 A | | 11/1998 | Eyal | 562/580 |
| 5,945,560 A | * | 8/1999 | Iffland et al. | 560/205 |
| 5,959,144 A | | 9/1999 | Baniel | 562/580 |
| 5,980,696 A | * | 11/1999 | Parten et al. | 203/1 |
| 6,087,532 A | | 7/2000 | Baniel et al. | 562/580 |
| 6,160,173 A | | 12/2000 | Eyal et al. | 562/589 |
| 6,187,951 B1 | * | 2/2001 | Baniel et al. | 562/580 |
| 6,280,985 B1 | | 8/2001 | Caboche et al. | 435/139 |
| 6,489,508 B1 | | 12/2002 | Van Gansbeghe et al. | 562/589 |

OTHER PUBLICATIONS

Co–pending U.S. Appl. No. 09/809,649; Entitled: "Azeotropic Distillation Process for Producing Organic Acids or Organic Acid Amides"; filed: Mar. 15, 2001.

Co–pending U.S. Appl. No. 09/809,534; Entitled: "Azeotropic Distillation of Cyclic Esters of Hydroxy Organic Acids"; filed: Mar. 15, 2001.

International Search Report for PCT/US02/06924, mailed Jul. 17, 2002.

* cited by examiner

PROCESS FOR OBTAINING AN ORGANIC ACID FROM AN ORGANIC ACID AMMONIUM SALT, AN ORGANIC ACID AMIDE, OR AN ALKYLAMINE ORGANIC ACID COMPLEX

BACKGROUND OF THE INVENTION

1. Field of the Invention

The present invention relates generally to processes for producing and recovering organic acids, such as lactic acid. More particularly, it concerns methods that rely on azeotropic distillation for production and recovery of organic acids from a feed stream comprising an organic acid amide, an organic acid ammonium salt, or an alkyl amine-organic acid complex.

2. Description of Related Art

Organic acids such as lactic acid have a number of commercial uses, for example in food manufacturing, pharmaceuticals, plastics, textiles, and as starting materials in various chemical processes. The current market in the United States for a particular organic acid, lactic acid, is about 50,000 tons per year, more than half of which is imported. It is well known to produce organic acids by fermentation of sugars, starch, or cheese whey, using microorganisms such as *Lactobacillus delbrueckii* to convert monosaccharides such as glucose, fructose, or galactose, or disaccharides such as sucrose, maltose, or lactose, into organic acids such as lactic acid. The broth that results from fermentation contains unfermented sugars, carbohydrates, amino acids, proteins, and salts, as well as the acid. Some of these materials cause an undesirable color or can interfere with downstream processing of the organic acid. The acid usually therefore must be recovered from the fermentation broth and in some cases must undergo further purification before it can be used.

Lactic acid and other α-hydroxyacids exist in two different optical isomers. For the example of lactic acid, these isomers are L-(+)-lactic acid and D-(-)-lactic acid. An equal mixture of D and L lactic acids is called a racemic mixture. It is often desirable to produce lactic acid with a high proportion of only one of the optical isomers. Different microorganisms used in fermentations to produce organic acids can produce different proportions of optical isomers of a particular organic acid. Chemical synthesis to prepare a higher proportion of a particular optical isomer can be difficult. It is desirable to minimize reactions that lead to the conversion of L-(+)-lactic acid into D-(-)-lactic acid and vice versa, so called racemization reactions. Exposing lactic acid solutions to relatively high temperatures can increase certain racemization reactions.

During the production of an organic acid such as lactic acid by fermentation, the increasing concentration of the acid in the fermentation broth reduces the pH. As the pH decreases, the growth of the microorganism is inhibited and eventually stops, and therefore acid production stops. To prevent this, the pH of the fermentation broth typically is controlled by adding a base for neutralization, such as ammonia or a sodium or calcium base. However, one result of the addition of such a base is the formation of a salt of the acid (e.g., ammonium lactate). Therefore, it is often necessary to convert the salt to free acid or another form such as an ester, which subsequently can be converted to the free acid.

It is known in the art that alkylamine can be used to aid in the recovery of organic acids from fermentation broths or other streams comprising organic acids and their salts (e.g., hydrolyzed polylactide, among others) via extraction. These amines are thought to interact with organic acid in an organic phase (e.g., extract) to form what can be termed an alkylamine-organic acid complex. It is known in the art that both ion pair and hydrogen bond interactions occur between the organic acid and the amine in the alkylamine-organic acid complex. In certain cases, the solvent phase of such an extraction can, in addition to the alkylamine, also comprise a diluent such as an alkane or an aromatic species. The solvent phase of such an extraction can also optionally comprise an extraction enhancer such as 1-octanol, which can enhance the solubility of the alkylamine-organic acid complex in the solvent phase.

As noted above, the alkylamine can be used to aid in removing acids from an aqueous phase (e.g. a fermentation broth). Therefore, methods to produce the organic acid from the alkylamine-organic acid complex of such an extraction are desirable.

Lactic acid is one organic acid of particular interest today because of a great projected demand for use as a polymer feedstock, particularly for use in producing degradable plastics. It is also used in the pharmaceutical and food industries, in leather tanning and textile dyeing, and in making solvents, inks, and lacquers. Although lactic acid can be prepared by chemical synthesis, production of lactic acid by fermentation of starch, cane sugar, whey or certain other carbon sources is a less expensive method. The production of lactic acid by fermentation is most efficient at a pH range where the lactic acid is largely present as a salt. Thus recovery of pure lactic acid often requires conversion of the salt into free acid and additional purification steps. One method that is used in purification is the production of a lactate ester from the lactic acid or salt, followed by purification of the ester. Finally the ester is converted to the free acid.

Hydroxyacids, such as lactic acid, or diacids can be converted to polymers (e.g., polyesters). These polymers can be recycled via digestion using pressurized water, acid, base, or a combination of such treatments. The product of such digestion can be a mixture of organic acids, salts of organic acids, and amides of organic acids. This digested material, which can be recycled for use in other processes, can contain significant impurities and can require purification to recover the organic acids therein.

Additionally, during processing of ammonium salts of organic acids, there is a tendency for organic amides to form, for example lactamide is formed from lactic acid via the following reaction:

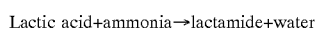

Lactic acid+ammonia→lactamide+water

There is a long standing need for improved processes for the production and recovery of relatively pure organic acids, particularly lactic acid, from feed streams comprising at least one of an organic acid amide, a alkyl amine-organic acid complex, and/or an ammonium salt of an organic acid.

SUMMARY OF THE INVENTION

The present invention is directed to an azeotropic distillation process for the recovery of an organic acid from a feed stream comprising at least one of an amide of organic acid, an ammonium salt of organic acid, or a alkylamine-organic acid complex. The organic acid of the amide, the ammonium salt, or the amine-organic acid complex has from 2 to 8 carbon atoms, and can be a mono-, di- or tri-carboxylic acid. Preferably, the organic acid is a hydroxy acid, more preferably it is lactic acid.

The process can be used in either a batch or a continuous mode. In either mode, a feed stream that comprises at least one of an organic acid amide, a alkyl amine-organic acid complex, or an ammonium salt of an organic acid is mixed with at least one azeotroping agent. The azeotroping agent can be a vapor or a liquid when it is mixed with the feed stream. ("Mixing" as used here refers to combining or contacting the feed stream and the azeotroping agent.) The at least one azeotroping agent is capable of forming at least one azeotrope, preferably a heteroazeotrope that comprises the azeotroping agent and the organic acid. Preferably the azeotroping agent is a hydrocarbon. In certain cases the azeotrope can further comprise water and/or the azeotroping agent can be capable of forming a second azeotrope consisting essentially of water and the azeotroping agent. The second azeotrope is preferably a heteroazeotrope.

While mixing the feed stream and the azeotroping agent, the mixture can be heated to produce a first vapor stream. Alternatively or in addition to heating the mixture, at least one of the feed stream or the azeotroping agent can be heated before they are mixed together. The heating produces a first vapor stream. The heating is sufficient to cause decomposition of at least one the organic acid ammonium salt, the organic acid amide, or the alkylamine-organic acid complex in the feed stream. The decomposition can occur when the feed stream and the azeotroping agent are contacted in a fractional distillation apparatus (e.g., column), such as a countercurrent fractional distillation apparatus. The first vapor stream comprises a first azeotrope that comprises the organic acid and the azeotroping agent. Preferably, the majority (e.g., greater than about 50 wt %) of the organic acid of the first azeotrope is a product of thermal decomposition of the organic acid ammonium salt, the organic acid amide, or the alkylamine-organic acid complex in the feed stream. Organic acid in the first azeotrope can also be organic acid that was present in the feed stream prior to heating. Preferably the first azeotrope is a heteroazeotrope. The first vapor stream can be separated producing a first bottoms stream. Preferably, this occurs while vacuum is being applied to the system. When the feed stream comprises at least one impurity, preferably the at least one impurity is at a lower concentration in the first vapor stream than in the feed stream. The first bottoms stream can be present as two phases, it can separate into two phases upon cooling, or it can exist as a single phase.

The first vapor stream can be condensed into a first liquid stream. The first vapor stream or the first liquid stream can undergo further distillation. In certain embodiments in which the first vapor stream comprises a first azeotrope that is a heteroazeotrope, the first liquid stream is capable of being separated into a first phase and a second phase. The first phase comprises the higher concentration of the organic acid and the second phase comprises the azeotroping agent. Removal of the first phase from the remainder of the first liquid stream, results in recovery of the organic acid. In certain embodiments, wherein the first azeotrope is not a heteroazeotrope (e.g. the azeotroping agent and the organic acid are miscible), the organic acid can be recovered from the single phase first liquid stream that is produced. The organic acid recovered in the first liquid stream (e.g. comprising a single phase or multiple phases) or in the removed first phase can be further purified and/or concentrated. Preferably the recovered organic acid has a lower concentration of impurities than the feed stream. It is also preferred that the recovered organic acid is heat stable. Furthermore, it is preferred that the recovered organic acid has a high degree of optical purity, preferably at least about 98% optical purity.

The organic acid recovered from the first liquid stream in this embodiment can come from any free organic acid initially present in the feed stream prior to heating and from the decomposition of the organic acid ammonium salt, the organic acid amide, or the alkylamine-organic acid complex. The first vapor stream can be condensed and collected (e.g. first liquid stream) and can then undergo further distillation(s) to further purify and/or condense recovered organic acid. Further distillation of the first liquid stream can, for example, result in removal of ammonia, which is more volatile than the azeotrope comprising the organic acid. Thus, the organic acid remaining in the first liquid stream after such distillation can comprise less ammonia.

In one embodiment, the feed stream comprises at least an ammonium salt of the organic acid to be recovered and little or essentially no water (e.g., less than about 10 wt % water). With this embodiment, the heating used in the process is sufficient to cause thermal decomposition of the ammonium salt to produce ammonia and the organic acid, and to cause vaporization of ammonia and of the first azeotrope comprising the organic acid and the azeotroping agent. The decomposition can be done in a countercurrent fractional distillation apparatus. Preferably the first azeotrope is a heteroazeotrope. The first liquid stream, which comprises the first azeotrope, can also comprise ammonia, which can optionally be distilled from the first liquid stream, as well as some or all water (if present) in the first liquid stream (e.g. by distillation of a binary second azeotrope which is preferably a heteroazeotrope).

Thus, this embodiment, which is directed to a process of thermal decomposition of an ammonium salt of an organic acid, results in the production of an organic acid that is recovered by azeotropic distillation. Similarly certain embodiments involve processes of thermal decomposition of an organic acid amide or an alkylamine-organic acid complex and azeotropic distillation resulting in the production of an organic acid. Certain embodiments can also result in recovery of organic acid with fewer impurities than were initially present in the feed stream comprising the organic acid.

Removal of impurities can be accomplished when impurities present in the feed stream are less volatile than the azeotrope comprising the organic acid and the azeotroping agent. Thus while heating the mixture of the azeotroping agent and the feed stream to produce a first vapor stream, the organic acid (e.g. a product of the thermal decomposition of its ammonium salt) that undergoes azeotropic distillation is separated from impurities that remain behind in the first bottoms stream. For example, sugars, or salts (like sodium chloride) which are thermally stable at the temperature required for thermal decomposition of the ammonium salt of the organic acid and vaporization of the azeotrope can be left behind in the first bottoms stream.

Embodiments of the present invention can involve different types of contacting modes for mixing feed streams (e.g., azeotroping agent and lactic acid feed stream). The feed streams can both be liquids, or one feed stream can be a liquid, while the other is a vapor.

In certain embodiments in which the feed stream comprises a hydroxyacid, water can be added to the feed stream in an amount sufficient to at least partially suppress formation of oligomers of the hydroxyacid.

In a batch mode, it is possible to distill off impurities that are more volatile prior to distillation of the first azeotrope or alternatively, when the impurities are less volatile than the first azeotrope, the impurities can remain behind, as the organic acid is azeotropically distilled off. Furthermore, certain impurities are expected to form their own azeotropes with the azeotroping agent, and the separation thus becomes a separation of one azeotrope from another. For example, pyruvic acid can be an impurity present in an organic acid ammonium salt feed stream. If the azeotroping agent forms an azeotrope with pyruvic acid and another azeotrope with the organic acid being purified, and the two azeotropes have different boiling points (e.g., the pyruvic acid azeotrope has a lower boiling point than that of the organic acid azeotrope), the pyruvic acid can be separated from the organic acid via azeotropic distillation of the pyruvic acid azeotrope. Specifically a pyruvic acid/dodecane azeotrope can be distilled overhead, while a lactic acid/dodecane azeotrope with a higher boiling point remains behind as a bottoms distilling stream.

Thus the present invention can provide relatively simple and cost-effective recovery of organic acid from feed streams that comprise at least one of an organic acid amide, an organic acid ammonium salt, or alkylamine-organic acid complex.

DESCRIPTION OF ILLUSTRATIVE EMBODIMENTS

Figure 1:
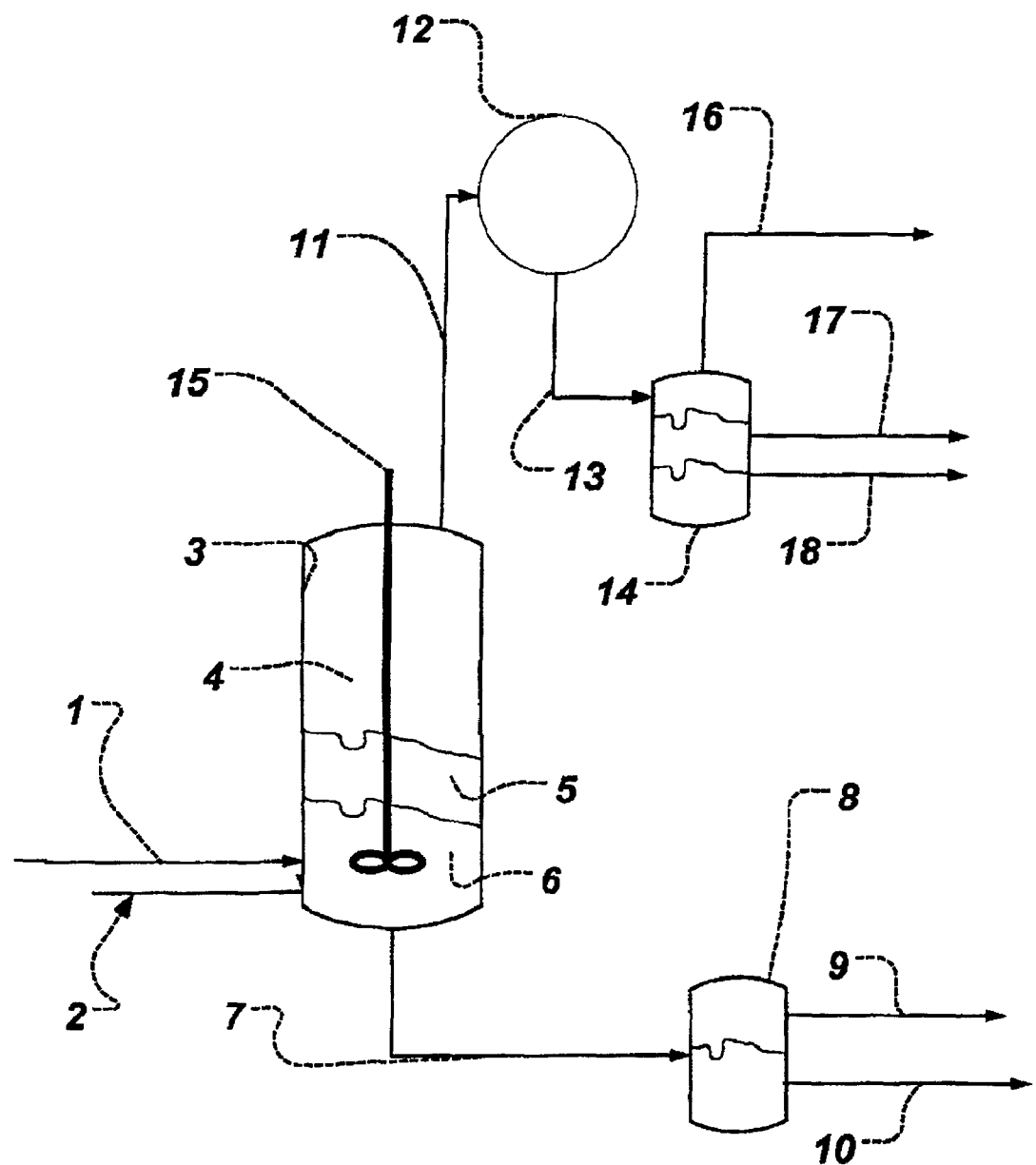
FIG. 1 is a process flow diagram in accordance with certain processes of the present invention for recovery of an organic acid.

The following definitions are useful in understanding the description of the present invention.

"Lactic acid" refers to the monomeric free lactic acid as is commonly found is dilute aqueous solutions. "88% lactic acid" and "lactic acid of commerce" refer to a typical commercially available lactic acid, which is actually a mixture of monomeric lactic acid, linear dimer lactic acid or lactoyl lactic acid, short chain lactic acid oligomers, water, and also a small quantity of cyclic dimer lactic acid or lactide. When this lactic acid is diluted in a large excess of water, it will slowly hydrolyze or convert to all monomeric form lactic acid. When concentrated lactic acid is diluted with water to a 50 wt % concentration, it will slowly hydrolyze to a mixture that is largely monomeric lactic acid, but which can still contain about 3 to 4 wt % dimer lactic acid, and trace amounts of higher oligomers.

"Organic acid amide" is defined here as an amide derived from reaction of ammonia with an organic acid. It is the preferred that the organic acid amide is not a secondary or tertiary amide produced by the reaction of one or two amine compounds with an organic acid. Organic acid amides herein can be species such as acetamide or lactamide or other amides. Note that lactamide can be present as optically pure L-lactamide, optically pure D-lactamide, or a mixture containing varying proportions of the D and L isomers.

"Azeotrope" and "azeotropic" are used herein to refer to systems that contain true azeotropic mixtures as well as those that are substantially azeotropic in nature (e.g., wherein the weight percentage of each component in the mixture in the liquid phase differs from the weight percentage of that same component in the vapor phase by no more than about 5 wt %, preferably by no more than about 2 wt %, more preferably by no more than about 1 wt %).

A "binary azeotrope" is an azeotrope that involves primarily two chemical compounds, and similarly, a "ternary azeotrope" is an azeotrope that involves primarily three chemical species.

A "heteroazeotrope" is an azeotrope that comprises more than one liquid phase.

A "binary heteroazeotrope" is an azeotrope that comprises more than one liquid phase and involves primarily two species of chemical compounds.

A "ternary heteroazeotrope" is an azeotrope that comprises more than one liquid phase and involves primarily three chemical species.

The "optical purity" of an α-hydroxyacid is defined as the molar ratio of one optical isomer to the total level of both isomers. For species that form oligomers and short and long chain polymers, the optical purity can be measured and expressed on a basis after the oligomers and polymers have been converted to monomers.

A "racemic lactic acid mixture" is defined as an equal mixture of D and L lactic acid optical isomers. An organic acid recovered using methods of the present invention is deemed "heat stable" if a sample of the separated first phase (or third phase, in certain embodiments), as defined above, can be concentrated (e.g. less than 5 wt % water) by heating at a temperature of up to about 140° C., and then heating the concentrate to 180° C. and holding it at 180° C. for two hours without color forming. Color formation under these conditions occurs when certain impurities are present, particularly when certain impurities often found in fermentation broths are present.

"Diethylbenzene" herein refers to either mixed isomers (1, 4-diethylbenzene, 1, 3-diethylbenzene, and 1, 2-diethylbenzene) or a single pure diethylbenzene isomer.

"Liquid extractant" refers to a composition comprising an alkylamine, as defined below, for use in extracting an organic acid from a fluid. The liquid extractant can optionally also comprise a diluent and/or an enhancer.

"Alkylamine" refers to water-immiscible organic extractant comprising at least one secondary or tertiary amine, in which the aggregate number of carbon atoms is at least 20, or a mixture of two or more such amines. Such alkylamines used in extracting organic acids are known in the art.

"Diluent" refers to an inert chemical species that can be used as a component of a liquid extractant that comprises an alkylamine for reasons such as to lower the viscosity of the extractant, to increase selectivity of the extractant against other unwanted species, or as a general purpose diluent. This is well known in the art of solvent extraction. A diluent can be a pure or mixed aromatic or aliphatic hydrocarbon. Diluents can be linear or branched chemical species. Examples of diluents that can be used with alkylamine liquid extractants include xylene, toluene, decane, dodecane, kerosene, and mixtures thereof.

"Enhancer" refers to a chemical species that can be a component of a liquid extractant and that acts to enhance the performance of the alkylamine extraction. The enhancer can strengthen the amine:organic acid complex and/or help solubilize the amine:organic acid complex. Use of enhancers in extraction of acids is known in the art. Examples of enhancers that can be used include polar species selected from alcohols, diols, ketones, diketones, fatty acids, chlorinated species, and other species known in the art. Preferably the ratio of the enhancer to the alkylamine in the liquid extractant is between about 1:10 and 1:1.

"Decomposition" as used herein refers to a process that results in the production of ammonia and organic acid from an organic acid ammonium salt, and in the production of amine and organic acid from an organic acid amide or a alkylamine-organic acid complex.

The feed stream that is mixed with the azeotroping agent comprises at least one of an amide of organic acid, an ammonium salt of organic acid, or a alkylamine-organic acid complex. The organic acid of the amide, the ammonium salt, or the amine-organic acid complex has from 2 to 8 carbon atoms, and can be a mono-, di- or tri-carboxylic acid. Preferably, the organic acid is a hydroxy acid, more preferably it is lactic acid. The feed stream can comprise a fermentation broth, an impure fluid comprising an organic acid amide, an impure fluid comprising an organic acid ammonium salt, an impure fluid comprising a mixture of organic acid amide and organic acid ammonium salt, or the feed stream can comprise an extract that comprises a alkylamine-organic acid complex produced by extraction of a fermentation broth or impure fluids. Specific examples of impure fluids that can be used as the feed stream include an aqueous solution of ammonium lactate that has impurities, or a lactamide solution that comprises impurities.

Feed streams comprising an ammonium salt of an organic acid or an organic acid amide can comprise a fermentation broth that is unpurified or at least partially purified. Production of an organic acid (e.g., lactic acid) and organic acid ammonium salts (e.g., ammonium lactate) by fermentation is well known. A person skilled in the art will be familiar with reactants, equipment, and process conditions suitable for such fermentation. The result of the fermentation will be an aqueous broth that comprises the organic acid, salts of the organic acid (including ammonium salts), in addition to other organic salts, inorganic salts, protein fragments, sugar residues, other organic acids, alcohols, ketones, and metal ions. Preferably, the feed stream of the present invention comprises a fermentation broth. The broth can be partially purified, for example by filtration or centrifugation, to remove some of the impurities. At least about 75 wt % of the whole cells and cellular debris has been removed in a partially purified fermentation broth. In certain embodiments it is preferred that the broth also be concentrated. Furthermore the fermentation broth can also be acidified prior to being used as a feed stream in the present invention.

Furthermore the fermentation broth can also be de-cationized, that is, alkali and alkaline monovalent, divalent and trivalent cations are to a large extent removed and replaced with the hydronium (H+) ion prior to being used as a feed stream in the present invention. Preferably all the alkali and alkaline monovalent, divalent and trivalent cations are exchanged. This cation exchange is performed using a solid or liquid ion exchanger primarily in the hydrogen form. One example of such a solid ion exchange resin is the Amberlite IR-120H+resin (Rohm and Haas).

Furthermore, the broth can be partially purified in one or several other ways known in the art before treatment in this process. Furthermore, the broth can be additionally purified or concentrated further after treatment by this invention.

Feed streams comprising an alkylamine-organic acid complex can comprise the extract (i.e. solvent phase) of an extraction of a fermentation broth or other stream comprising an organic acid and optionally salts (e.g., hydrolyzed polylactide, among others) performed with a liquid extractant that comprises an alkylamine. The alkylamine-organic acid complex is present in the extracted organic phase, which can be separated from the aqueous phase that comprises water and water-soluble components of the fermentation broth or impure fluid stream. The organic phase can also be purified with a small amount of acid or water prior to using the organic phase as a feed stream in the present invention. The alkylamine of the complex is preferably trilaurylamine As noted above, in certain embodiments the liquid extractant used to in the extraction can further comprise an extraction enhancer in addition to the alkylamine. For example, if the organic acid that is to be recovered is lactic acid, the fermentation broth or impure fluid comprising lactic acid and ammonium lactate can be extracted with tri-n-octylamine (e.g., alkylamine) and octyl-lactate (extraction enhancer), resulting in a tri-n-octylamine-lactic acid complex. The fermentation broth or fluid comprising organic acid in an ammonium salt, amide or complex that is extracted can be concentrated and/or purified prior to extraction. For example the fermentation broth can be purified using ion exchange chromatography prior to extraction with a alkylamine.

Certain embodiments of the present invention involving thermal decomposition of a trialkylamine-organic acid complex, followed by azeotropic distillation of the organic acid and azeotroping agent can be expressed using the following equation:

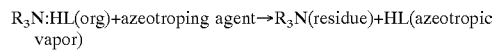
$R_3N{:}HL(org)+\text{azeotroping agent} \rightarrow R_3N(\text{residue})+HL(\text{azeotropic vapor})$ $R_3N{:}HL$ is a trialkylamine-organic acid complex in an extract (e.g. organic phase) used as a feed stream. The azeotropic vapor comprises the azeotroping agent and the organic acid (HL). The amine ($R_3N$) is a product of the thermal decomposition of the complex and in this case, the amine remains as a residue in the bottoms.

In certain embodiments, the decomposition and the azeotropic distillation can be expressed using the following equation:

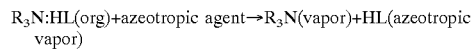
$R_3N{:}HL(org)+\text{azeotropic agent} \rightarrow R_3N(vapor)+HL(\text{azeotropic vapor})$ In the process described by this equation, both the amine (i.e. base) and the organic acid are vaporized. The vapor stream comprising the amine and the organic acid can undergo further separation directly, or the vapor stream can first be condensed followed by further distillation. $R_3N$ can be a volatile primary amine, a secondary amine, or ammonia.

In certain embodiments, the feed stream can comprise an organic acid amide that undergoes thermal decomposition and azeotropic distillation. The amide can be produced through reaction of $R_3N$ and an organic acid from an extract that has undergone at least some decomposition of the amine:organic acid complex. For the example of lactic acid, the feed stream can comprise lactamnide or $CH_3$—CHOH—CO—$NH_2$ that was produced from an extract. In this case, the azeotroping agent ideally comprises a hydrocarbon and at least some water. The process as it occurs with lactamide can be expressed using the following equation:

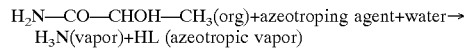
$H_2N$—CO—CHOH—$CH_3$(org)+azeotroping agent+water→ $H_3N$(vapor)+HL (azeotropic vapor)

Alternatively, the feed stream can comprise amides produced by reaction of (a) organic acids with ammonia or (b) organic acid esters with ammonia, or by heating of organic acid ammonia salts. Formation of organic acids amides from organic acids in the presence of ammonia is well known in the art. Thus, for example, a fermentation broth comprising an ammonium salt of an organic acid can be thermally treated resulting in the formation of amides of the organic acid, and the thermally treated fermentation broth can be used as a feed stream in the present invention. Preferably, the organic acid amide that the feed stream is comprised of is an amide of a hydroxy acid, more preferably it is lactamide.

As stated above, the feed stream can be derived from sources other than fermentation. For example, the feed stream can comprise products, like salts of organic acids and organic acid amides that result from the digestion of a organic acid polymer (e.g. polylactide). The feed stream can comprise a product produced by treating a polyester, wherein the product comprises at least one of organic acids, organic acid ammonium salts, organic acid amides, or mixtures thereof.

Certain embodiments of the present invention can be better understood by reference to FIG. 1. In an embodiment of the present invention run in the batch mode, a batch charge of feed stream 1 is made to reactor 3. The feed stream 1 comprises at least one of an organic acid amide, an organic acid ammonium salt, or a alkylamine-organic acid complex, as described above. In certain embodiments, the feed stream 1 can further comprise free organic acid. Preferably the organic acid that is to be recovered is selected from the group consisting of organic acids having from 2 to 8 carbon atoms and is a monocarboxylic, dicarboxylic or tricarboxylic acid. More preferably the organic acid is a hydroxy organic acid that has from 2 to 6 carbon atoms. Furthermore, the hydroxy organic acid can be an alpha, beta, delta, gamma, or epsilon hydroxy acid. The organic acid can be selected from the group consisting of lactic acid, pyruvic acid, beta-hydroxybutyric acid, hydroxyacetic acid, glycolic acid, propionic acid, and acetic acid, among others. Preferably the organic acid is lactic acid. It is preferred that the organic acid that is recovered using processes of the present invention is heat stable, more preferably the recovered organic acid is a heat stable lactic acid. In certain embodiments, it is preferred that the recovered organic acid is an alpha hydroxy acid that is at least about 98% optically pure.

Preferred organic amides that can be present in the feed stream in certain embodiments and which can be thermally decomposed to recover organic acid include lactamide, pyruvamide, beta-hydroxy butyramide, propionamide, and acetamide, among others. The ammonium salts that are present in feed streams of certain embodiments are ammonium salts of the organic acids described above.

The alkylamine-organic acid complexes that can be present in the feed stream can be obtained by extraction of an organic acid containing fluid with a liquid extractant comprising an alkylamine. The solvent phase of the extraction (e.g. comprising the liquid extractant and extracted organic acid) can be used as the feed stream or as a component of the feed stream of the present invention. The liquid extractant preferably comprises at least one water-immiscible secondary or tertiary alkylamine, in which the aggregate number of carbon atoms is at least 20, or a mixture of two or more such amines. Examples of alkylamines that can be components of the liquid extractant are trilaurylamine and tri-n-octylamine, among others. The liquid extractant can comprise a diluent and/or an extraction enhancer in addition to the alkylamine. Examples of suitable extraction enhancers are alcohols, diols, ketones, diketones, fatty acids, chlorinated species, and other species known in the art. The diluent used in preparing an extract (e.g. solvent phase of an extraction) that is used as a component of a feed stream (comprising alkylamine-organic acid complex) in the present invention can be 1) a substantially pure chemical species that is identical to the azeotroping agent, such that the azeotroping agent is an essentially pure hydrocarbon; 2) a significantly higher boiling chemical species than the azeotroping agent, such that the diluent does not enter the azeotropic distillation train, or 3) a significantly lower boiling species than the azeotroping agent.

Consider the extraction of a lactic acid solution with a liquid extractant comprising an alkylamine, wherein an extract (e.g., solvent phase) is produced that comprises alkylamine-lactic acid complex. The extract can be used as a feed stream in the present invention, undergoing thermal decomposition followed by azeotropic distillation of the organic acid. In certain embodiments, dodecane can be used as a diluent in the extraction (e.g., a component of the liquid extractant). When the solvent phase of the extraction is used as the feed stream, the dodecane serves as the azeotroping agent in the azeotropic distillation for the recovery of the lactic acid. In certain other embodiments octadecane can be used as the diluent in extraction. When the extract comprising the octadecane, the alkylamine, and the lactic acid is used as a feed stream and dodecane is used as an azeotroping agent in azeotropic, the octadecane remains as a bottoms stream, while the lactic acid is distilled overhead azeotropically along with dodecane. Alternatively hexane can be used as a diluent for the amine extraction, and the extract can be used as a feed stream and dodecane can be used as the azeotroping agent. The hexane is distilled overhead and can be removed before the azeotropic distillation of the dodecane and lactic acid. In certain embodiments a feed stream comprising an alkylamine-organic acid complex can be fed to the bottom of the fractional distillation apparatus or reactor 3. Alternatively, a feed stream comprising an alkylamine-organic acid complex can be fed to the middle of the fractional distillation apparatus 3 and the azeotroping agent 2 can be fed to the bottom of the fractional distillation apparatus 3, and there is reflux in upper half of the fractional distillation apparatus 3.

A batch charge comprising at least one azeotroping agent 2, is also made to the reactor 3. Azeotroping agents used in methods of the present invention are selected so that they are capable of forming at least one first azeotrope that comprises the azeotroping agent and the organic acid that is to be recovered from the feed stream 1. Preferably the first azeotrope is a heteroazeotrope. Embodiments of the present invention can involve (i) a single first azeotrope that is binary (e.g. consisting essentially of the organic acid and the azeotroping agent 2), (ii) a single first azeotrope that is ternary (e.g. consisting essentially of the organic acid, water, and the azeotroping agent), or (iii) more than one first azeotrope (e.g. one that is binary and another that is ternary). In certain embodiments, the azeotroping agent can be capable of forming a second azeotrope comprising water that does not comprise the organic acid. Preferably the second azeotrope is a heteroazeotrope. If essentially no other chemical species are part of the second azeotrope, it can be a binary azeotrope.

Preferably, the at least one azeotroping agent is a hydrocarbon having a boiling point of between about 100° C. less than and 150° C. more than the boiling point of the organic acid that is being recovered (e.g. the boiling points as compared at the same pressure). More preferably, the azeotroping agent has a boiling point of between about 50° C. less than and 50° C. more than the organic acid boiling point.

The azeotroping agent can in certain embodiments be a hydrocarbon having 7 to 14 carbon atoms, especially those embodiments involved in the recovery of lactic acid. Hydrocarbons used as azeotroping agents can be either aromatic or aliphatic, and aliphatic hydrocarbons can be branched, unbranched or cyclic. Examples of hydrocarbons suitable for use as azeotroping agents in certain embodiments (especially those for the recovery of lactic acid) include diethylbenzene, dodecane, decane, octylbenzene, propylbenzene, and ethylbenzene, among others. Preferably the azeotroping agent used in recovering lactic acid is diethylbenzene, octylbenzene or dodecane, more preferably diethylbenzene. The azeotroping agent can be, in certain embodiments, an ether, for example an ether having from 7 to 16 carbon atoms. Ethers used as azeotroping agents can be either aliphatic or aromatic. Examples of ethers that can be used as azeotroping agents in certain embodiments (especially those for the recovery of lactic acid) include dimethylene glycol dimethyl ether and dipropylene glycol dimethyl ether, among others.

In certain embodiments, more than one azeotroping agent can be used, for example benzene and cyclohexane can be used as azeotroping agents with a feed stream that yields acetic acid upon thermal decomposition of an ammonium acetate or acetamide present in the stream. Acetic acid, benzene, and cyclohexane form a ternary azeotrope, and acetic acid and benzene form a binary azeotrope. Both the binary and ternary azeotropes are heteroazeotropes and can be used in certain embodiments of the present invention to recover acetic acid through an azeotropic distillation in which acetic acid is recovered from a feed stream.

The two batch charges 1 (e.g. feed stream) and 2 (e.g. azeotroping agent) are not fully miscible and two liquid phases 5 and 6 are observed. A stir bar 15 is added to the reactor 3 and stirred at sufficient speed to create a turbulent interface and some dispersion of droplets of phase 6 into phase 5. This causes a vortex, but does not completely mix the two phases. There are several possible alternatives for mixing (e.g. contacting) the azeotroping agent 2 and the feed stream 1 in the present invention. For example, the azeotroping agent that is mixed with the feed stream can be in the form of a vapor. When the azeotroping agent is introduced as a vapor, the azeotroping agent and the feed stream can be mixed with one another in a column or they can be mixed with one another in a flash reactor. Furthermore, the mixing of the azeotroping agent and the feed stream can be done in a countercurrent fashion (e.g., utilizing a countercurrent fractional distillation apparatus).

Heat is applied to reactor 3 and a first vapor stream 11 comprising the first heteroazeotrope (e.g. comprising azeotroping agent and organic acid) travels from the reactor headspace 4 to condenser 12. Heat can be applied through the use of a reboiler or other using other devices known in the art. Alternatively or in addition to heating the mixture in the reactor 3, at least one of the feed stream 1 or the azeotroping agent 2 can be heated before they are mixed together. The heat is sufficient to cause thermal decomposition of at least one of the organic acid amide, the organic acid ammonium salt or the alkylamine-organic acid complex in the feed stream 1. The heat is also sufficient to vaporize the first azeotrope, but preferably the heat is also not so high as to cause significant degradation or side reaction of the products (e.g. greater than 50 wt % of products degraded or reacted). In certain embodiments a vacuum can be applied to aid in the removal of the vapors from the reactor headspace 4. In certain embodiments, the reactor 3 can be a countercurrent fractional distillation apparatus, such as countercurrent column.

The preferred temperature range in the reactor 3 is related to: (a) the boiling points of the azeotroping agent, the first azeotrope, and impurities, (b) the temperature necessary to achieve thermal decomposition to produce organic acid, as well as (c) the system pressure and the concentrations of organic acid amide, organic acid ammonium salt, alkylamine-organic acid complex and/or water in the feed stream. The preferred temperature range for heating the mixture in the present invention is between about 100° C. and 240° C. As an example, when using dodecane as an azeotroping agent with a feed stream comprising 80 wt % ammonium lactate or lactamide and a system pressure of −22.4 mm Hg, the temperature is preferably between about 140° C. to 170° C. Other factors affecting the selection of an appropriate system temperature are known in the art. For example, whether the process is being run in batch or continuous mode can influence the choice of appropriate system temperatures. If run in the continuous mode the type of equipment used in the process can be a further consideration (e.g. whether a stripper column or a continuous stirred tank reactor (CSTR) is used). Heating of the reaction can be accomplished using methods known in the art. The system pressure is typically held constant. In certain embodiments it is preferred that the process is carried out at about atmospheric pressure (e.g., about 12.7 to 16.7 psia). The condensate 13 (e.g. first liquid stream) enters into receiver 14, where it can be separated into phases 17 (e.g. second phase) and 18 (e.g. first phase). Samples of the first phase 18 and of the second phase 17 can be periodically removed after separation of the two phases. The organic acid is recovered in the first phase 18. Generally, the second phase 17 will comprise the azeotroping agent(s). When the azeotroping agent has a lower density than the first phase that comprises the recovered organic acid, it forms the upper phase of the first liquid stream 13 from the first vapor stream 11. Diethylbenzene is used as the azeotroping agent in an example below. Diethylbenzene has a lower density than the first phase (phase comprising the recovered organic acid). After the first vapor stream 11 is removed and condensed to a first liquid stream 13, the diethylbenzene can separate on top of the first phase 18, and is therefore referred to as the light phase in the example that follows. The first phase 18 is referred to as the heavy phase in the examples. However, relative positions of the first phase 18 and second phase 17 can vary depending on their relative densities.

There are two temperature probes in the vapor space, one located above the reactor liquid 5 and 6 in the reactor headspace 4 and another in the vapor space at the system head prior to the condenser 12. Bottoms residue stream 7 can be removed from reactor 3 to a receiver 8. In certain embodiments, the first bottoms stream 7 can be separated into phases 9 and 10 in the receiver 8. Phase 9 generally comprises the azeotroping agent, while phase 10 comprises the heavy phase bottoms (e.g. comprising organic acid amide, ammonium salt of an organic acid, lactic acid oligomers or alkylamine-organic acid complex).

The organic acid is recovered when the first phase 18 is separated and removed. Preferably the recovered organic acid has a lower concentration of impurities than the feed stream. It is also preferred that the recovered organic acid is heat stable, and in certain embodiments the organic acid is preferably an alpha hydroxy acid that is optically pure. After separation and removal of the first phase 18 from the second phase 17, the recovered organic acid can be further purified and/or concentrated. Residual azeotroping agent present in the first phase 18 can be stripped from it, or the separated first phase 18 can be subjected to further distillation operations to separate various impurities or azeotropes that it comprises.

Separation and removal of the azeotroping agent from liquid streams comprising heteroazeotropes can be conducted using systems known in the art for purifying a heterogeneous azeotrope comprising an aqueous phase and an azeotroping agent. For example, when separating the two phases of a first liquid stream, two columns can be used that are both served by a common liquid-liquid decanter. The bottoms from one column after distillation can be purified organic acid, while the bottoms from the other column can be purified azeotroping agent. When recovering reactive organic acids, such as hydroxyacids, such a system can optionally be run at reduced pressure (e.g. between about 1 and 10 psia) to avoid or reduce the formation of oligomers. The contacting mode can be such that residence times are limited to reduce extent of oligomer formation. Optionally, water can be introduced at certain points in the process to suppress formation of oligomers. Subsequently, and optionally, water can be stripped from recovered azeotroping agent or recovered organic acid or amide using a water strip agent or other method as part of the recovery process.

If the azeotroping agent boils below the boiling point of the organic acid, then the azeotroping agent can be readily separated from the phase comprising the recovered organic acid by using stripping type distillation that is known in the art.

In some instances the first phase 18 with recovered organic acid can be integrated into another industrial process. For example a separated first phase 18 with recovered lactic acid that resulted from an azeotropic distillation with diethylbenzene as the azeotroping agent provides a feed for other processing steps as described in the co-filed application, "Azeotrope Distillation of Cyclic Esters of Hydroxy Organic Acids", Ser. No. 09/809,534. Thus, in certain embodiments, the separated and removed first phase may not need to be stripped of residual azeotroping agent or of certain other compounds, if they either do not interfere with downstream processing or actually provide a benefit to subsequent processes.

As an alternative to the batch method described above, the process can be run in the continuous mode, wherein there can be a continuous feed of feed stream 1 into reactor 3 and a continuous feed of azeotroping agent 2 into reactor 3. Furthermore the azeotroping agent from phases 9 and/or 17 can in certain embodiments (run either in batch or continuous mode) be recycled for use in a continuous process or in subsequent batch or continuous processes of the present invention. Still further, in certain embodiments, phase 10 (e.g. the phase of the first bottoms stream comprising the organic acid, amide, complex or salt thereof) can also be recycled as part of the feed stream 1 for a continuous process or for subsequent batch or continuous processes.

The present invention provides means for recovering the organic acid from the fermentation broth. However, it should be understood that the present invention is not limited to use in conjunction with fermentation broth. For example, phase 10 of the bottoms (the undistilled liquid in the reactor 3 after removal of first heteroazeotrope comprising organic acid) can be used in a feed stream. Preferably, phase 10 (comprising organic acid amide, ammonium salt or complex of an organic acid that failed to be azeotropically distilled off) of the first bottoms stream used as feed stream is the result of a previous batch mode azeotropic distillation of the organic acid. In other instances, the feed stream can be derived from other sources. The feed stream used in the present invention comprises a stream of an organic acid amide or an ammonium salt thereof, or both.

Additionally, the invention can be used to recover lactic acid from recycled polylactide polymer, polylactic acid polymer, or polyesters comprising lactic acid or other hydroxy acids. For example, a crude shredded polymer can be treated with a heated aqueous phase to hydrolyze some or all of the polymer and the resultant stream can then be used as a feed stream to one of the embodiments of this invention. Alternatively, said polymer can be treated with an ammonia containing stream that will act to increase the rate and extent of hydrolysis of the polymer prior to or simultaneously with one of the azeotropic distillation embodiments presented here.

Additionally, the invention can be run in equipment that limits the contact time of the feed stream and the azeotroping agent, such as a vapor-liquid contactor. Selection of devices and methods that limit the duration of high temperature and of contact are well known in the art. Equipment such as wiped film evaporators, nitrogen swept reactors or columns, and low holdup packed distillation systems can be used. Certain embodiments of the present invention can limit the rate and extent of racemization or the organic acid that is recovered regardless of whether equipment that limits duration of high temperature and contact is used. (See example 4 below.) Selection of devices and methods that limit the duration of high temperature and of contact are well known in the art. Equipment such as wiped film evaporators, nitrogen swept reactors or columns, and low holdup packed distillation systems can be used. Furthermore process conditions can be modified as desired, for example reduced pressure can be used in processes of the present invention.

As stated above, methods of the present invention can be run in a continuous mode or in a batch mode. When run in continuous mode the feed stream 1 and the at least one azeotroping agent 2 are introduced as continuous feeds. In certain embodiments in which the method is practiced in a continuous mode, it is preferred that a periodic or small, continuous purge of heavy impurities in the first bottoms stream of the reaction chamber be performed. Reflux steps can be used in methods of the present invention, but are not required.

Certain embodiments of the present invention involve a "dry" feed stream comprising an ammonium salt or amide of the organic acid to be recovered, and little or essentially no water, preferably the ammonium salt is ammonium lactate and the amide is lactamide. The ammonium salt or amide of the organic acid is present in the feed stream at a concentration of between about 50 wt % and 95 wt %. Preferably the feed stream used in such embodiments comprises less than about 10 wt % water, more preferably less than about 5 wt % water. Preferably when the feed stream comprises organic acid ammonium salt, it further comprises at least about 0.5 moles of ammonium per mole of total organic acid ("total organic acid" as used herein is defined as the sum of free organic acid, oligomers, ammonium salts thereof, and other salts thereof present in the feed stream). In certain embodiments, the feed stream for this first case can further comprise free organic acid in addition to the ammonium salt or amide of the organic acid, but free acid need not be present. When free organic acid is present in a feed stream comprising organic acid ammonium salt, the molar ratio of the ammonium salt of the organic acid to the free acid can be as high as about 1:1. With this embodiment, the heating used in the process is sufficient to aid thermal decomposition of the ammonium salt or amide. In the embodiments in which organic acid ammonium salts are decomposed, heating is sufficient to produce ammonia and the organic acid, and to cause vaporization of ammonia and of at least one azeotrope comprising the organic acid and the azeotroping agent. Preferably the at least one azeotrope is a heteroazeotrope. Furthermore, in certain embodiments, the azeotroping agent can act as heat carrier for the thermal decomposition of the ammonium salt or amide of the organic acid. Thus, the organic acid recovered from methods of this first embodiment can come from any free organic acid initially present in the feed stream prior to heating and from the decomposition of the ammonium salt or amide of the organic acid.

In certain variations of this embodiment, the operation can be performed in two or more distillation columns in series. In one variation, the crude feed comprising an organic acid ammonium salt is fed as a liquid to a mid-column feed location in the first distillation column, and azeotroping agent is fed as a liquid or vapor to a lower region of the column. Organic acid, azeotroping agent, ammonia, and light impurities are taken overhead from this distillation column as a first vapor stream. Heavy impurities are left as the first bottoms stream of this first column. The first vapor stream is then fed to a second distillation column and is separated into a second overhead vapor stream that comprises ammonia, water, and light impurities, and a bottoms stream that comprises purified organic acid. Optionally, additional water or azeotroping agent can be introduced to the second column.

Figure 2:
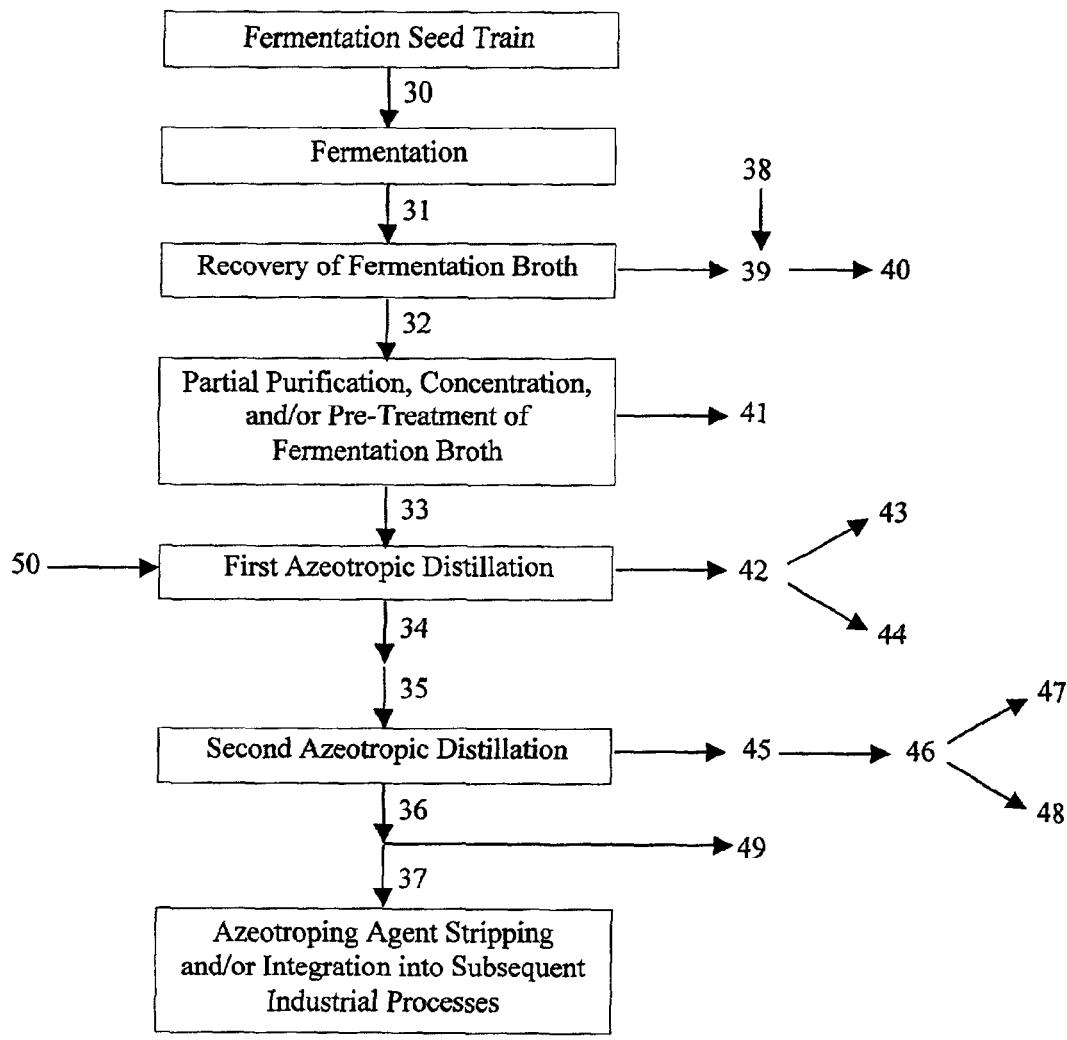
FIG. 2 is a flow diagram in accordance with certain processes of the present invention that comprise at least two azeotropic distillations.

As stated above, the first liquid stream recovered from a first azeotropic distillation of an organic acid can undergo additional distillation to increase purity and/or concentration of the organic acid or amide. A schematic of a process implementing further distillation is diagrammed in FIG. 2. A fermentation seed stock 30 is generated using a fermentation seed train. The fermentation seed stock 30 is introduced into the scaled up fermentation for the production of organic acid along with fresh nutrients, water, and a carbon source. Methods of fermentation are known in the art. After fermentation the cell culture 31 can comprise organic acid, organic acid salts (e.g., ammonium salts of organic acids), organic amide, cells, cellular debris, fermentation products, impurities (e.g. other organic acids and salts, among others), water, and unused carbon source. The cell culture 31 is then processed to recover the fermentation broth 32. Cells and cellular debris 39 can be removed by filtration or centrifugation. The fermentation broth 32 can then undergo partial purification and/or pre-treatment prior to decomposition and a first azeotropic distillation. Partial purification can, for example, comprise precipitation and removal of certain impurities. Preferably the fermentation broth is concentrated by removal of water and solvents 41 produced by fermentation. The concentrated, pre-treated fermentation broth 33 can comprise organic acid or amide and at least about 20 wt % water.

The concentrated, pretreated fermentation broth 33 is mixed with an azeotroping agent 50 (e.g. diethylbenzene) and the mixture is heated to cause decomposition of at least one of organic acid ammonium salt, organic acid amide, or alkylamine-organic acid complex to produce a first vapor stream 34 and a first bottoms stream 42, as part of the first azeotropic distillation. The first azeotropic distillation can involve a first column or other fractional distillation apparatus, and the mixing of the feed stream of azeotroping agent 50 and the feed stream 33 can occur in the column or other fractional distillation apparatus. The first vapor stream 34 comprises a first azeotrope comprising organic acid and the azeotropic agent and can further comprise water vapor. Preferably the first azeotrope is a heteroazeotrope. Preferably the organic acid in the first azeotrope is the product of decomposition of at least one of organic acid ammonium salt, organic acid amide, or alkylamine-organic acid complex in the feed stream 33. The first vapor stream 34 is condensed to a first liquid stream 35. The first liquid stream 35 can, in certain embodiments, comprise at least about 20 wt % water, organic acid or amide and the azeotroping agent.

In cases in which the azeotroping agent is capable of forming a binary second azeotrope, consisting essentially of water and the azeotroping agent, the process can further comprise a second azeotropic distillation of the first liquid stream 35. Preferably the second azeotrope is a heteroazeotrope. The second azeotropic distillation can be performed using a second column or other fractional distillation apparatus, and involves heating and mixing the first liquid stream 35 to produce a second vapor stream 45 and a second bottoms stream 36. The second vapor stream 45 is separated from the first liquid stream 35, producing the second bottoms stream 36. The second vapor stream 45 comprises a second azeotrope consisting essentially of water and the azeotroping agent. The second bottoms stream 36 that remains after removal of the second vapor stream 45, can comprise water or azeotroping agent, and can be a vapor, a liquid or both, and the second bottoms stream can be condensed into a liquid which can be separated into a third phase 37 and a fourth phase 49. The third phase 37 comprises a higher concentration of the organic acid than the fourth phase 49, and the fourth phase 49 comprises the azeotroping agent. The organic acid or amide can be recovered by separation and removal of the third phase 37 from the fourth phase 49.

The third phase can, optionally, be further purified and/or concentrated. For example residual azeotroping agent can be stripped from the third phase 37. Alternatively if components other than the organic acid or amide are present in the third phase that will not interfere with downstream processing, the entire third phase 37 can be used in subsequent industrial processes. Preferably the recovered organic acid in the third phase 37 is heat stable, and in certain embodiments it is preferred the organic acid is an alpha hydroxy acid that at least about 98% optically pure. It is also preferred that the recovered organic acid has a lower concentration of impurities than was present in the feed stream.

The by-products of this double azeotropic distillation should be noted. First, regarding the cellular material 39 removed from the cell culture 31, water or aqueous media 38 can be added to cellular material 39 and washed cells 40 can be recovered. Depending on the nature of the washed cells and cellular material 40, they can be further processed as components in other processes or products.

Furthermore, the first bottoms stream 42 of the first azeotropic distillation can, optionally, be separated into two phases 43 and 44. Phase 43 comprises unused azeotroping agent and phase 44 can comprise undistilled organic acid salt or amide, along with certain impurities. Both phases can be recycled in subsequent azeotropic distillations. For example, water can be added to phase 44 to hydrolyze oligomers of organic acid and it can be re-used as a feed stream, and the azeotroping agent of phase 43 can also be recycled in subsequent azeotropic distillations. Likewise, the second vapor stream 45 of the second distillation comprising the second azeotrope (consisting essentially of water and azeotroping agent) can be condensed to a second liquid stream 46 that can be separated into two phases 47 and 48, when the second azeotrope is a heteroazeotrope. Phase 47 comprises azeotroping agent, and phase 48 comprises water. The azeotroping agent in phase 47 can be recycled for subsequent azeotropic distillation processes. Likewise, the fourth phase 49 comprising azeotroping agent can be recycled.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Addition of 95% Ammonium Lactate Aqueous Droplets to Hot N-dodecane Liquid in Flash Decomposition A feed comprising ammonium lactate that had previously been analyzed by Karl Fisher analysis, ammonia electrode and HPLC and was found to contain the compositions shown below in the Table 1 along with small amounts of impurities like pyruvic acid and a compound eluting at about the same retention time as oxalic acid. Despite care being taken to minimize lactamide formation in this 95 wt % ammonium lactate feed stream (e.g., the ammonium lactate was prepared at neutral pH using a continuous controlled metered feed of cold lactic acid and ammonia, using evaporation under reduced pressure, and benzene azeotropic drying under reduced pressure) there was still about 1.59 wt % lactamide present in this feed stream. However, analysis has shown that lactamide can be present even in unprocessed fermentation broth at low levels (e.g., 0.3 wt % of total lactic acid values).

N-dodecane (about 50 ml) was heated to 155.0° C. and stirred. The ammonium lactate feed prepared as described above was added drop wise over 5 minutes with a total of about 1.8 grams added. The mixture was stirred and held at 155° C. for 60 minutes. No visible flashing or steaming was noted.

TABLE 1

| | FEED 95% ammonium lactate ppm (mg/kg) | BOTTOMS PRODUCT After Liquid Flash Decomposition ppm (mg/kg) |
|---|---|---|
| Lactic acid | 784,068 | 384,600 |
| Lactamide | 15,917 | 455,300 |
| Lactic Dimer | 30,294 | 57,500 |
| Lactic Trimer | 1,140 | 3,390 |
| Water (Karl Fisher) | 47,712 | 4,000 (approx) |
| Ammonia as NH4+ (electrode) | 123,000 | 32,000 |

The process resulted in the mixture containing a viscous phase that adhered to the bottom of the stainless steel beaker that it had been heated and mixed in. Based on an ammonia analysis of the residue, and the overall mass balance, it appeared that there was about 80 wt % removal of ammonia. About 27 wt % of the ammonia was removed in overhead vapors, while about 53 wt % of the ammonia was converted to new lactamide that was not present at the start of the run. About 20 wt % of the ammonia was not removed from the system. The final water content was about 0.4 wt %. Salt solutions provide significant boiling point elevation, and water is strongly attracted to ammonium lactate, and thus it would be unlikely to obtain a concentrated lactic acid/ammonium lactate solution with less than 0.4 wt % water at an exit temperature of 160° C. Lactic dimer and trimer levels increased 2-fold and 3-fold, respectively in the bottoms product relative to their amounts in the feed stream.

HPLC analysis was used to analyze the bottoms products. Oxalic acid and pyruvic acids can be present as impurities in both the feed and in the bottoms. Other processes, such as distillation of lactic acid under vacuum and azeotropic distillation, are designed in part to remove these impurities. Both oxalic acid and pyruvic acid are low pH acids and can be removed via selective ion exchange. Other degradation products, such as formic acid or acetaldehyde or reaction products of acetaldehyde with lactic acid were not detected.

EXAMPLE 2

Figure 3:
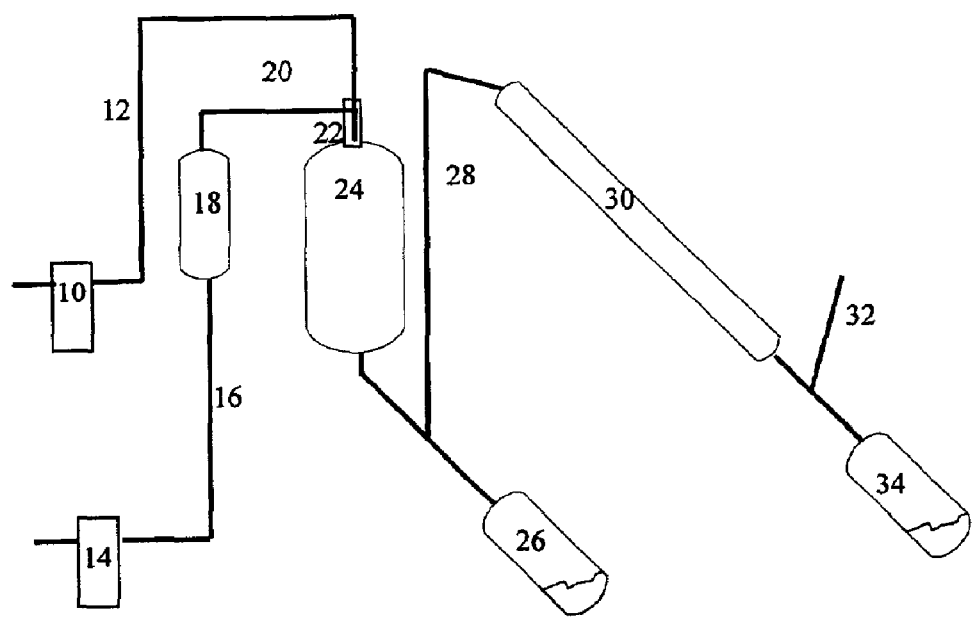
FIG. 3 is a process flow diagram in accordance with certain processes of the present invention for recovery of an organic acid.

Addition of Ammonium Lactate Droplets to Hot Condensing Diethylbenzene Vapors in Flash Decomposition The same equipment was used for Examples 2 and 3 and a schematic of the equipment is depicted in FIG. 3. The system was built entirely from stainless steel and can be operated at pressures from full vacuum to 400 psig and up to 240° C. A feed stream pump 10 is used to feed 90–95 wt % ammonium lactate 12 to the flash reactor 24. A solvent stream pump 14 is used to feed solvent 16 to a solvent boiler 18. The solvent is heated to a temperature of about 30° C. higher than the boiling point of the solvent. The solvent vapor 20 is brought into contact with the droplets of the ammonium lactate feed stream at 22. The ammonium lactate and solvent mixture 22 is heated in the flash reactor 24 to achieve thermal decomposition of the ammonium lactate. The liquids bottoms from the flash reactor are collected in the receiver 26. Vapor from the flash reactor goes through the vapor riser 28 and the condenser 30. The condensed vapor (e.g., overhead from the flash reactor) is collected in the receiver 34. A vent line and trap 32 is positioned between the condenser 30 and the receiver 34.

The ammonium lactate stream 12, and 22 is not significantly preheated until it enters the flash reactor 24. A stream of $N_2$ is used to purge the equipment prior to startup and also at shutdown to reduce any potential for explosion. The electrical heaters can be set to temperature control or power level control. Temperature is recorded using 4 thermocouples: one located on the boiler jacket 18, one in the boiler vapor stream 20, one in the vapor riser 28, and one on the vapor riser shell 28. The thermocouples are type K and accurate to about 1° C.

In Example 2, a feed comprising 90 wt % ammonium lactate 12 was fed continuously at a rate of 0.535 gram/minute liquid using a metering pump 10 to a flash chamber 24. Simultaneously, hot vaporized mixed isomers of diethylbenzene (solvent) 20 were introduced at a feed rate of 4.14 gram/minute, as vapor into the flash chamber 24. The residence time in the flash chamber 24 was about 4 seconds. The temperature was about 175° C. in the flash reactor and the pressure about 14.7 psia. The combined vapor and liquid streams were led out of the bottom of the flash chamber 24 and the vapor was drawn off as an overhead vapor stream 28 and condensed 30. The overhead vapor separated into two liquid phases in the receiver 34. The heavy or lower liquid phase was found to comprise about 5 molar lactic acid and 8 molar ammonia. There was significant lactic acid dimer in the feed stream, present as the ammonium salt, but no lactic acid dimer was detected in the condensed overhead vapor heavy liquid phase. This showed that there was no entrainment.

EXAMPLE 3

Addition of Ammonium Lactate Droplets to Hot Condensing Hexadecane Vapors in Flash Decomposition This example was performed similarly to Example 2, but with hexadecane as the solvent instead of diethylbenzenes.

The temperature and pressure of the flash reactor were maintained at about 205° C. and 15 kPaa. About 32.9% of the ammonia was removed. Some of the lactic acid (about 4.8 wt %) released by thermal decomposition of ammonium lactate was converted to new lactamide that was not originally present in the ammonium lactate feed stream. The bottoms stream 26 had a water content of about 1.27 wt %. The bottoms heavy phase was very viscous and flowed poorly at 20° C. This example showed that it is possible to simultaneously decompose ammonium lactate into ammonia and free lactic acid, to take the ammonia into the vapor phase, and to also take lactic acid into the vapor phase and leave behind heavy impurities in the bottoms phase.

EXAMPLE 4

Thermal Decomposition of Tri-n-octylamine-lactic Acid Complex Prepared by Extraction of a Dilute, Untreated Fermentation Broth, via Flash Azeotropic Distillation with N-dodecane under Reduced Pressure A batch charge of 350 g n-dodecane (467 mL, Fisher Scientific, catalog # 001294) was made to a 500-mL three-neck flask, which was attached to a standard vacuum distillation system via a 1"×10" column, filled 6" high with Pro-Pak stainless steel dump-packing (Ace Glass, Inc., catalog # 6624-04). A constant vacuum of 22.4 in Hg was provided by a membrane pump. A cold trap immersed into an isopropanol/dry ice bath (−78° C.) was installed between the primary (water-cooled) condenser and the vacuum pump to condense any vapors escaping from the distillation system. Heating was provided by a 500-mL heating mantle, controlled by an autotransformer (50% power output). The flask and column were well insulated against heat loss. Stirring was provided by means of a magnetic stirrer/hotplate and a Teflon-coated magnetic stirring bar in the flask. Moderate heating was also provided by the hotplate to compensate for heat loss through the heating mantle. The temperature of the liquid phase (T1) and the vapor phase at the head of the column (T2) was measured by appropriately positioned thermocouples, and was monitored throughout the experiment. A tri-n-octylamine-lactic acid extract was pumped through a stainless steel tube into the column one inch above the packing. A constant feed flow rate of 14.1 g/h was maintained by a metering pump. Before addition of the feed started, a stable n-dodecane vapor flow was established by preheating the system. The liquid condensate collected in this phase of the experiment was separated from the following main fraction, which also contained lactic acid. When the batch charge of n-dodecane was depleted in the flask, a constant n-dodecane feed was also applied.

The tri-n-octylamine-lactic acid feed was prepared by extracting a dilute (4.9%), untreated lactic acid fermentation broth with tri-n-octylamine (Acros Organics, lot # A010982001). Extraction was performed in two steps, first shaking 80 mL broth with 20 mL of tri-n-octylamine for 30 sec and then shaking 80 mL of fresh broth with the extract obtained in the first step. The second extract was washed with 10 mL of n-dodecane before distillation.

Decomposition of the tri-n-octylamine-lactic acid complex was carried out at 151° C. (T2), while the temperature in the boiler was maintained at 165° C. (T1), giving a temperature gradient of about 14° C. along the column. As the distillation proceeded, formation of small drops of a colorless heavy oily looking substance (lactic acid) was observed in the primary condenser, which was carried forward slowly by the much larger amounts of condensed n-dodecane into the receiver. Toward the end of the experiment, however, the accumulated concentrated lactic acid developed a light rusty color, which is believed to be a result of corrosion of the steel packing. Lactic acid was recovered by carefully washing the condenser and condensed n-dodecane with 60 mL of deionized water. The colorless washings were combined and analyzed by HPLC on a 300×7.8 mm Aminex HPX-87H (BioRad) ion exclusion column at room temperature, using 0.00919% $H_2SO_4$ as the mobile phase at 0.6 mL/min flow rate. HPLC separation of compounds in samples was detected using either a ultraviolet (UV) or refractive index (RI) detector. The lactic acid content of the feed was determined by extracting 1 mL of the amine complex with 2 mL of 1 N NaOH solution, neutralizing the aqueous phase with 2 mL of 1 N HCl, and analyzing the resultant solution by liquid chromatography as described above.

A total of 28.9 g tri-n-octylamine-lactic acid complex was fed into the column at a flow rate of 14.1 g/h. On the basis of liquid chromatography analysis, it contained 5.16 g lactic acid as lactic acid monomer equivalent (18% by weight). The aqueous washings of the distilled material contained 4.75 g lactic acid as L1 (e.g. monomeric lactic acid) equivalent, which gives 92% isolated yield. Distillation of this amount of lactic acid was carried out with 347 g of n-dodecane, or 73 g n-dodecane per gram lactic acid monomer, which is indicative of the energy required for distillation. The final lactic acid product was of 7.8% concentration by weight.

Impurities in the lactic acid broth and product on 88% lactic acid basis included small amounts of maleic acid, oxalacetic acid, pyruvic acid, malic acid, formic acid, acetic acid, along with other impurities that were not identified. Some of the unidentified impurities appear to be the same impurities (have the same retention times) as impurities that are found in commercially available 88% lactic acid.

The broth, prior to extraction, contained a ratio of D-lactic acid to total lactate of 0.02%. The product after extraction and azeotropic decomposition contained a ratio of D-lactic acid to total lactate of 0.05%. Thus optical purity is conserved in this process. This is surprising, as it is known that bases and cations can act as promoters of racemization.

TABLE 2

| | | UV detection: | | |
|---|---|---|---|---|
| RETENTION TIME (MIN) | Peak Assignment | Concentration in the broth | Concentration in W12-OV2H sample | Comments |
| 9.3 | Lactic acid (dimeric form) | undetected | 31.76 g/L | |
| 9.8 | Lactic acid (trimeric form) | 1.35 g/L | 5.79 g/L | |

TABLE 2-continued

UV detection:

| RETENTION TIME (MIN) | Peak Assignment | Concentration in the broth | Concentration in W12-OV2H sample | Comments |
| --- | --- | --- | --- | --- |
| 11.6 | Lactic acid (monomeric form) | 1057 g/L | 1012 g/L | |
| 16.8 | Lactamide | trace | trace | Present in all commercial acids |

TABLE 3

RI detection:

| RETENTION TIME (MIN) | Peak Assignment | Concentration in the broth | Concentration in W12-OV2H sample | Comments |
| --- | --- | --- | --- | --- |
| >6 | Solvent | — | — | |
| 7.0 | Maltose | 13.7 g/L | undetected | Completely rejected |
| 8.4 | Glucose | 4.45 g/L | undetected | Completely rejected |
| 12.6 | Glycerol | 4.78 g/L | undetected | Completely rejected |

EXAMPLE 5

Thermal Decomposition of Tri-n-octylamine-lactic Acid Complex, Prepared by Extraction of a Concentrated, Pretreated Fermentation Broth, via Flash Azeotropic Distillation with N-dodecane under Reduced Pressure A batch charge of 160 g n-dodecane (213 mL, Fisher Scientific, catalog # 001294) was made to a 250-mL three-neck flask, which was attached to a standard vacuum distillation apparatus via a 1"×10" column, filled 6" high with Pro-Pak stainless steel dump-packing (Ace Glass, Inc., catalog # 6624-04). A constant vacuum of 22.4 inHg was provided by a membrane pump. A cold trap immersed into an isopropanol/dry ice bath (−78° C.) was inserted between the primary (water-cooled) condenser and the vacuum pump to condense any vapors escaping from the system. Stirring was provided by means of a magnetic stirrer/hotplate and a Teflon-coated stirring bar in the flask. Heating was provided by a 250-mL heating mantle, controlled by an autotransformer. The flask and column were insulated well against heat loss. Moderate heating was also provided by the hotplate to compensate heat loss through the heating mantle. The temperature of the liquid phase (T1) and the vapor phase at the head of the column (T2) was measured by appropriately positioned thermocouples, and was monitored throughout the experiment. The tri-n-octylamine-lactic acid complex was fed through a stainless steal cannula into the column, 1' above the packing. Before addition of the feed started, a stable n-dodecane vapor flow was established. The condensate collected in this phase of the experiment was separated from the following main fraction, which also contained lactic acid.

The tri-n-octylamine-lactic acid feed was prepared by extracting a concentrated (39.5%) and ion-exchanged lactic acid fermentation broth with tri-n-octylamine (Acros Organics, lot # A010982001). Extraction was performed in two steps, first shaking 5 mL broth with 10 mL of amine for 30 sec and then shaking 5 mL of fresh broth with the extract obtained in the first step. The second extract was washed with 10 mL of n-dodecane before distillation.

Decomposition of the tri-n-octylamine-lactic acid complex was carried out at 153° C. (T2), while the temperature in the boiler was maintained at 166° C. (T1), giving a temperature gradient of about 13° C. along the column. The experiment produced a small amount of pink colored oil in the primary condenser, but no heavy phase could be distinguished visually in the receiver. In order to recover the lactic acid product, the condenser and receiver were carefully washed with 10 mL of deionized water each. The colorless washings were analyzed separately by HPLC on a 300×7.8 mm Aminex HPX-87H (BioRad) ion exclusion column at room temperature, using 0.00919% $H_2SO_4$ as the mobile phase at 0.6 mL/min flow rate. The lactic acid content of the feed was calculated as the difference between that of the starting broth and that left in the two raffinates after extraction.

A total of 5.19 g extract was fed into the column at a flow rate of 7.8 g/h. It contained 1.75 g lactic acid as lactic acid monomer equivalent (33% by weight). The combined aqueous washings of the distilled material contained 1.34 g lactic acid as lactic acid monomer equivalent, which gives 77% isolated yield. Distillation of such amount of lactic acid was carried out with 112 g of n-dodecane, or 83 g n-dodecane per gram lactic acid, which is indicative of the energy required for distillation. The final lactic acid solutions were of 8% (washings from the receiver) and 5% (washings from the condenser) concentration by weight.

EXAMPLE 6

Thermal Decomposition of Trilaurylamine-lactic Acid Complex Prepared by Extraction of a Concentrated, Pretreated Fermentation Broth via Flash Azeotropic Distillation with N-dodecane under Reduced Pressure A batch charge of 340 g n-dodecane (453 mL, Acros, lot # B0501185) was made to a 500-mL three-neck flask, which was attached to a standard vacuum distillation apparatus via a 1"×10" column, filled 8" high with borosilicate glass helices (Aldrich, Inc., catalog # Z41,195-7). A constant vacuum of 23.6 inHg was provided by a membrane pump. A cold trap immersed into an isopropanol/dry ice bath (−78° C.) was inserted between the primary (water-cooled) condenser and the vacuum pump to capture any vapors escaping from the system. Heating was provided by a 500-mL heating mantle, controlled by an autotransformer. The flask and column were well insulated against heat loss. Stirring was provided by means of a magnetic stirrer/hotplate and a Teflon-coated stirring bar in the flask. Moderate heating was also provided by the hotplate to compensate heat loss through the heating mantle. The temperature of the liquid phase (T1) and the vapor phase at the head of the column (T2) was measured by appropriately positioned thermocouples, and was monitored throughout the experiment by a PC. The trilaurylamine-lactic acid complex, containing lauryl lactate enhancer, was fed by a metering pump at a constant flow rate through a stainless steel tube into the column, 1" above the packing. It was preheated to 125° C. before entering the column by means of an oil bath. Prior to addition of the feed started, a stable n-dodecane vapor flow was established by preheating the system. The liquid condensate collected in this phase of the experiment was separated from the following main fraction, which also contained lactic acid.

The trilaurylamine-lactic acid feed was prepared by extracting a concentrated (44.2%), ion-exchanged lactic acid fermentation broth with a 1:1 molar mixture of trilaurylamine (Alamine 304-1, Henkel, lot # 8F155) and lauryl lactate (ISP Van Dyk, Inc., lot # VE 1117). Extraction was performed in two steps, first shaking 20 mL broth with 80 mL of amine for 2 min and then shaking 20 mL of fresh broth with the extract obtained in the first step. The second extract was backwashed with three times with 2 mL of deionized water before distillation.

Decomposition of the trilaurylamine-lactic acid complex was carried out at 148° C. (T2). The temperature of n-dodecane in the flask was 158° C. (T1) at the beginning, but steadily increased to about 195° C. as the amount of trilaurylamine-lauryl lactate increased. As the distillation proceeded, formation of small drops of a colorless heavy oil (lactic acid) was observed in the primary condenser, which was carried forward slowly by the much larger amounts of condensed n-dodecane into the receiver. Two fractions were collected in this phase of the experiment (second and third overhead samples), both consisting of heavy and light phases: The second sample had a total weight of 116.4 g; the third one had a total weight of 153.9 g. Lactic acid was recovered by carefully washing the condenser and condensed n-dodecane with 20 mL of deionized water. Washings from the condenser were added to the third overhead fraction. The colorless washings were combined and analyzed by HPLC on a 300×7.8 mm BioRad Organic Acid column at room temperature, using 0.00919% $H_2SO_4$ as the mobile phase at 0.6 mL/min flow rate. The lactic acid content of the feed was determined by extracting 1 mL of the amine complex with 5 mL of 0.1 N NaOH solution, neutralizing the aqueous phase with 5 mL of 0.1 N HCl, and analyzing the resultant solution by liquid chromatography as described above.

A total of 46.1 g amine extract was fed into the column at a flow rate of 27.7 g/h. On the basis of liquid chromatography analysis, it contained 6.36 g lactic acid as lactic acid monomer equivalent (13.8% by weight). The aqueous washings of the two distillation fractions contained a total of 7.51 g lactic acid as lactic acid monomer equivalent, which gives 117.7% isolated yield. The excessive yield suggests that at least 18% of the recovered lactic acid originated from the lauryl lactate enhancer, either via transesterification with lactic acid or via hydrolysis with extracted water. The second and third overhead samples contained 2.02 g and 5.48 g lactic acid, respectively. Distillation of such amounts of lactic acid required 114 g and 149 g of n-dodecane, respectively. The energy of distillation can be expressed as the ratio of the weight of n-dodecane and lactic acid, which is 42 on average. The concentration of lactic acid in the two aqueous solutions was of 9% and 22% by weight, respectively.

Impurities in the lactic acid broth and product on 88% lactic acid basis included small amounts of maleic acid, oxalacetic acid, pyruvic acid, malic acid, formic acid, acetic acid, along with other impurities that were not identified. Some of the unidentified impurities appear to be the same impurities (have the same retention times) as impurities that found in commercially available 88% lactic acid.

TABLE 4

| | | UV detection: | | | |
|---|---|---|---|---|---|
| RETENTION TIME (MIN) | Peak Assignment | Concentration in the broth | Concentration in W47-OV2H sample | Concentration in W47-OV3H sample | Comments |
| 9.3 | Lactic acid (dimeric form) | 13.57 g/L | 59.86 g/L | 63.80 g/L | |
| 9.8 | Lactic acid (trimeric form) | 1.18 g/L | 2.81 g/L | 3.65 g/L | |
| 11.6 | Lactic acid (monomeric form) | 1036 g/L | 985.5 g/L | 979.6 g/L | |
| 16.8 | Lactamide | 0.74 g/L | | 0.31 g/L | Present in all commercial acids |
| ~20 | Ethyl lactate | 1.07 g/L | trace | trace | Uncertain identity, minor impurity |

TABLE 5

| RETENTION TIME (MIN) | Peak Assignment | Concentration in the broth | Concentration in W47-OV2H sample | Concentration in W47-OV3H sample | Comments |
|---|---|---|---|---|---|
| >6 | Solvent | — | — | — | |
| 7.0 | Maltose | 20.0 g/L | undetected | undetected | Completely rejected |
| 8.4 | Glucose | 8.75 g/L | undetected | undetected | Completely rejected |
| 12.6 | Glycerol | 14.65 g/L | undetected | undetected | Completely rejected |

RI detection:

EXAMPLE 7

Thermal Decomposition of Tri-n-octylamine-lactic Acid Complex via Batch Azeotropic Distillation with Diethylbenzene Under Atmospheric Pressure A batch charge of 40 g diethylbenzene (46 mL, Acros Organics, lot # A012667201) and tri-n-octylamine-lactic acid complex, prepared separately from 2 mL of 90% commercial L-lactic acid (Pfanstiehl, lot # 22776), 2 mL of water, and 10 mL of tri-n-octylamine (Acros Organics, lot # A010982001), was made to a 100-mL three-neck flask which was attached to a standard vacuum distillation apparatus. The flask contained two liquid phases at this point. Stirring was provided by means of a magnetic stirrer/hotplate and a Teflon-coated stirring bar in the flask. Heating was provided by a heating mantle, controlled by an autotransformer. The flask and distillation head were insulated well against heat loss. Moderate heating was also provided by the hotplate to compensate heat loss through the heating mantle. The temperature of the liquid phase (T1) and the vapor phase at the distillation head (T2) was measured by appropriately positioned thermocouples.

Decomposition of the tri-n-octylamine-lactic acid complex was carried out by heating the above mixture from room temperature to 171° C. (T1). During the distillation T2 reached a maximum of about 95° C. (T1=130° C.) and then decreased steadily as the flow of distillate decreased, despite further increase of T1. Two overhead fractions were collected, both consisting of heavy and light phases. The first fraction was collected at T1 <130° C., while T2 reached the maximum 95° C. It had a total volume of 2.1 mL, of which 1.45 mL was aqueous phase. The second fraction was collected at 130° C.<T1<171° C. and had a total volume of 1.3 mL, of which 0.7 mL was aqueous phase. Although the bulk of the initial solution was still in the boiler at T1=171° C., practically no distillate was received at this point. This remaining solution was found to be homogeneous. The colorless aqueous phases were separated from diethylbenzene in the overhead fractions and analyzed by HPLC on a 300×7.8 mm Jordi Gel Organic Acid column at room temperature, using 0.085% $H_3PO_4$ containing 10% acetonitrile as the mobile phase at 1.4 mL/min flow rate.

On the basis of liquid chromatography analysis, the starting two-phase solution contained 2.16 g lactic acid as lactic acid monomer equivalent. The aqueous phases from the two overhead fractions contained a total of 19 mg lactic acid as lactic acid monomer equivalent, which gives only 0.9% isolated yield. The first fraction contained 12 mg, the second 7 mg lactic acid. These results suggest that decomposition of the tri-n-octylamine-lactic acid complex is low under such conditions. In fact, the small amount of lactic acid recovered could have originated from residual acid left in the raffinate due to the equilibrium nature of extraction. Distillation of the above amounts of lactic acid required 0.57 g and 0.52 g diethylbenzene, respectively, giving 47 and 74 as the weight ratio of diethylbenzene and lactic acid, which is suggestive of the energy of distillation. The concentration of lactic acid in the two aqueous solutions produced was 0.8% and 1% by weight, respectively.

EXAMPLE 8

Thermal Decomposition of Ammonium Lactate Via Batch Aazeotropic Distillation with Diethylbenzene Under Atmospheric Pressure A batch charge of 60 g diethylbenzene (69 mL, Acros a Organics, lot # A012667201) and 17 g of aqueous 69% ammonium lactate solution (Pfanstiehl, lot # 26415A) was made to a 100-mL three-neck flask, which was attached to standard vacuum distillation apparatus. The flask contained two liquid phases at this point. Stirring was provided by means of a magnetic stirrer/hotplate and a Teflon-coated stirring bar in the flask. Heating was provided by a heating mantle, controlled by an autotransformer. The flask and distillation head were insulated well against heat loss. Moderate heating was also provided by the hotplate to compensate heat loss through the heating mantle. The temperature of the liquid phase (T1) and the vapor phase at the distillation head (T2) was measured by appropriately positioned thermocouples.

Decomposition of ammonium lactate was carried out by heating the above mixture from room temperature to 181° C. (T1). By the end of distillation T2 reached a maximum of 173° C. Ten overhead fractions were collected, all consisting of heavy and light phases. Details about the overhead fractions are provided in the following Table.

TABLE 6

| Total volume (mL) | Weight of DEB (g) | Weight of heavy phase (g) | Temperature range (T2) |
|---|---|---|---|
| 4.9 | 2.175 | 2.364 | <95.5 |
| 5.1 | 1.653 | 3.030 | 95.5 |
| 5.2 | 3.306 | 1.344 | 95.5–158 |
| 5.5 | 4.507 | 0.317 | 158 |
| 5.7 | 4.437 | 0.593 | 158–163 |
| 5.5 | 4.576 | 0.238 | 163–165 |
| 5.2 | 4.35 | 0.225 | 165–169 |
| 5.5 | 4.655 | 0.162 | 169–171 |
| 7.2 | 6.020 | 0.305 | 171–172 |
| 7.7 | 6.542 | 0.194 | 172–173 |

During distillation a strong smell of ammonia was detected, indicating that decomposition of ammonium lactate took place and free ammonia escaped from the system. The residue of distillation still had two phases and the heavy phase had the appearance of a viscous oil. The colorless aqueous phases were separated from diethylbenzene in the overhead fractions and analyzed by HPLC on a 300×7.8 mm Jordi Gel Organic Acid column at room temperature, using 0.085% $H_3PO_4$ containing 10% acetonitrile as the mobile phase at 1.4 mL/min flow rate. The ammonia content of these solutions was also determined using a Cole-Palmer 27502-03 Ammonium Electrode.

On the basis of liquid chromatography and ammonia analysis, the starting solution contained 11.8 g (110 mmol) ammonium lactate and 95 mg (1.06 mmol) lactamide. The aqueous phases from the ten overhead fractions contained a total of 0.26 g (2.9 mmol) lactic acid as lactic acid monomer equivalent, 0.11 g (1.24 mmol) lactamide, as well as 0.51 g (30.1 mmol) ammonia. Ammonia analysis of the distillation residue gave only 0.09 g (5.27 mmol) ammonia, while liquid chromatography analysis showed 1.93 g (21.7 mmol) lactamide. These results suggest that 95% of the starting ammonium lactate decomposed under the applied conditions. About half of it escaped from the apparatus in the form of ammonia gas, one-third remained dissolved in water and was recovered in the overhead heavy fractions, and one-fifth was transformed into lactamide which did not distill. Our observations also suggest that decomposition of ammonium lactate occurred early and under moderately high temperatures in the distillation process, when the bulk of water was distilled in the form of diethylbenzene-water azeotrope. The first four overhead heavy fractions contained as much as 80% of the total "distilled" ammonia and 84% of water, but only 12% of lactic acid and 3% of lactamide. Most of the free ammonia gas evolved in this period as well. These fractions were collected at temperatures $T1<177°$ C. and $T2<157°$ C. More particularly, 60% of the "distilled" ammonia was recovered from the second and third overhead heavy phases, which distilled when the pot temperature (T1) was between 145 and 165° C.

Obviously, all the distilled lactic acid products contained enough ammonia to convert the acid back to ammonium lactate form, which had less than 3% of the starting mass. Thus, the bulk of lactic acid remained in the boiler in the form of viscous higher oligomers and ammonia-free lactic acid may be recovered from it via hydrolysis or saponification.

All of the methods disclosed and claimed herein can be made and executed without undue experimentation in light of the present disclosure. While the methods of this invention have been described in terms of preferred embodiments, it will be apparent to those of skill in the art that variations may be applied to the methods and in the steps or in the sequence of steps of the methods described herein without departing from the concept, spirit and scope of the invention. More specifically, it will be apparent that certain agents which are both chemically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A process for obtaining an organic acid from a feed stream comprising at least one of an organic acid ammonium salt, an organic acid amide, or a alkylamine-organic acid complex, comprising the steps of:

mixing a feed stream and at least one azeotroping agent, wherein the feed stream comprises at least one of an organic acid ammonium salt, an organic acid amide, or a alkylamine-organic acid complex, and wherein the organic acid of the salt, amide or complex is selected from the group consisting of monocarboxylic acids, dicarboxylic acids, and tricarboxylic acids having from 2 to 8 carbon atoms;

distilling the feed stream by a method comprising the steps of
   (i) heating at least one of the feed stream, the azeotroping agent, or the mixture of thereby (a) decomposing the ammonium salt, the amide, or the alkylamine-organic acid complex to produce organic acid and (b) producing a first vapor stream that comprises at least one first azeotrope comprising the organic acid and the at least one azeotroping agent; and
   (ii) separating the first vapor stream from the mixture.

2. The process of claim 1 wherein the decomposing is done in a countercurrent fractional distillation apparatus.

3. The process of claim 2, wherein the feed stream comprises an alkylamine-organic acid complex, and the feed stream is fed to the bottom of the fractional distillation apparatus.

4. The process of claim 2, wherein the feed stream comprises an alkylamine-organic acid complex, and the feed stream is fed to the middle of the fractional distillation apparatus, the at least one azeotroping agent is fed to the bottom of the fractional distillation apparatus, and there is reflux in the upper half of the fractional distillation apparatus.

5. The process of claim 1, wherein the heating is done using a reboiler.

6. The process of claim 1, wherein the first azeotrope is a minimum boiling azeotrope.

7. The process of claim 1, wherein the first azeotrope is a heteroazeotrope.

8. The process of claim 1, wherein the feed stream comprises at least one impurity, and wherein the at least one impurity is at a lower concentration in the first vapor stream than in the feed stream.

9. The process of claim 1, wherein the azeotroping agent comprises a hydrocarbon and at least some water.

10. The process of claim 1, further comprising producing a first bottoms stream as the first vapor stream is separated, wherein the first bottoms stream comprises at least one of an organic acid ammonium salt, an organic acid amide, or an alkylamine-organic acid complex.

11. The process of claim 1, wherein the first azeotrope is a heteroazeotrope and further comprising condensing the first vapor stream to form a first liquid stream, wherein the first liquid stream is capable of being separated into a first phase and a second phase, wherein the first phase comprises a higher concentration of organic acid than the second phase, and wherein the second phase comprises azeotroping agent.

12. The process of claim 11, further comprising separating the first liquid stream into a first phase and a second phase, wherein the first phase comprises a higher concentration of organic acid than the second phase, and wherein the second phase comprises the at least one azeotroping agent.

13. The process of claim 1, wherein the organic acid is selected from the group consisting of lactic acid, pyruvic acid, beta-hydroxybutyric acid, glycolic acid, propionic acid, and acetic acid.

14. The process of claim 1, wherein the feed stream comprises an organic acid amide selected from the group consisting of lactamide, pyruvamide, beta-hydroxybutyramide, propionamide, and acetamide.

15. The process of claim 1, wherein the feed stream comprises a hydroxy acid.

16. The process of claim 15, wherein the hydroxy acid is lactic acid.

17. The process of claim 1, wherein the feed stream comprises a hydroxyamide.

18. The process of claim 17, wherein the hydroxyamide is lactamide.

19. The process of claim 1, wherein the feed stream comprises a fermentation broth, wherein the fermentation broth comprises the organic acid ammonium salt, the organic acid amide, or the alkylamine-organic acid complex.

20. The process of claim 19, wherein the fermentation broth is concentrated prior to the mixing of the feed stream and the azeotroping agent.

21. The process of claim 1, wherein a vacuum is used in removing the first vapor stream from the mixture.

22. The process of claim 1, wherein the at least one first azeotrope further comprises water.

23. The process of claim 1, wherein the at least one azeotroping agent is a hydrocarbon having a boiling point of between about 100° C. less than and 150° C. more than the organic acid boiling point.

24. The process of claim 23, wherein the hydrocarbon has a boiling point of between about 50° C. less than and 50° C. more than the organic acid boiling point.

25. The process of claim 23, wherein the hydrocarbon has 7 to 14 carbon atoms.

26. The process of claim 25, wherein the hydrocarbon is selected from the group consisting of diethylbenzene, dodecane, decane, octylbenzene, propylbenzene, and ethylbenzene isomers.

27. The process of claim 25, wherein the hydrocarbon is aromatic or aliphatic.

28. The process of claim 27, wherein the aliphatic hydrocarbon is branched, unbranched, or cyclic.

29. The process of claim 1, wherein the feed stream comprises between about 50 wt % and 95 wt % ammonium salt of the organic acid.

30. The process of claim 29, wherein the ammonium salt is ammonium lactate.

31. The process of claim 29, wherein the feed stream comprises less than about 10 wt % water.

32. The process of claim 1, wherein the process is a continuous process.

33. The process of claim 1, wherein the process is a batch process.

34. The process of claim 1, wherein the at least one azeotroping agent that is mixed with the feed stream is a vapor.

35. The process of claim 34, wherein the mixing of the at least one azeotroping agent and the feed stream takes place in a column.

36. The process of claim 34, wherein the mixing of the at least one azeotroping agent and the feed stream takes place in a flash reactor.

37. The process of claim 34, wherein the mixing of the at least one azeotroping agent and the feed stream is countercurrent.

38. The process of claim 1, wherein the process is performed at about atmospheric pressure.

39. The process of claim 1, wherein the feed stream comprises a product produced by treating a polyester, wherein the product comprises at least one of organic acids, organic acid ammonium salts, organic acid amides, or mixtures thereof.

40. The process of claim 1, wherein the at least one azeotroping agent is an ether having from 7 to 16 carbon atoms.

41. A process for obtaining an organic acid from a feed stream comprising at least one of an organic acid ammonium salt, an organic acid amide, or a alkylamine-organic acid complex, comprising the steps of:

mixing a feed stream and at least one azeotroping agent, wherein the feed stream comprises at least one of an organic acid ammonium salt, an organic acid amide, or a alkylamine-organic acid complex, and wherein the organic acid of the salt, amide or complex is selected from the group consisting of monocarboxylic acids, dicarboxylic acids, and tricarboxylic acids having from 2 to 8 carbon atoms; and distilling the feed stream by a method comprising the steps of (i) heating at least one of the feed stream, the at least one azeotroping agent, or the mixture thereof, thereby a decomposing the ammonium salt, the amide, or the alkylamine-organic acid complex to produce organic acid, and (b) producing a first vapor stream that comprises at least one first azeotrope comprising the organic acid and the at least one azeotroping agent;

(ii) separating the first vapor stream from the mixture;

(iii) producing a first bottoms stream as the first vapor stream is separated, wherein the first bottoms stream comprises at least one of an organic acid ammonium salt, an organic acid amide, or an alkylamine-organic acid complex;

(iv) adjusting the temperature of the first vapor stream such that a second vapor stream that comprises a second azeotrope that comprises water and the at least one azeotroping agent is produced; and (v) separating the second vapor stream from the first vapor stream, thereby producing a second bottoms stream, wherein the second bottoms stream comprises organic acid.

42. The process of claim 41, wherein the second bottoms stream is a vapor, a liquid, or a vapor-liquid mixture.

43. A process for obtaining an organic acid from a feed stream comprising at least one of an organic acid ammonium salt, an organic acid amide, or a alkylamine-organic acid complex, comprising the steps of:

mixing a feed stream and at least one azeotroping agent, wherein the feed stream comprises at least one of an organic acid ammonium salt, an organic acid amide, or a alkylamine-organic acid complex, and wherein the organic acid of the salt, amide or complex is selected from the group consisting of monocarboxylic acids, dicarboxylic acids, and tricarboxylic acids having from 2 to 8 carbon atoms; and distilling the feed stream by a method comprising the steps of (i) heating at least one of the feed stream, the at least one azeotroping agent, or the mixture thereof, thereby (a) decomposing the ammonium salt, the amide, or the alkylamine-organic acid complex to produce organic acid, and (b) producing a first vapor stream that comprises at least one first azeotrope that is a heteroazeotrope comprising the organic acid and the at least one azeotrope agent;

(ii) separating the first vapor stream from the mixture;

(iii) condensing the first vapor stream to form a first liquid stream, wherein the first liquid stream is capable of being separated into a first phase and a second phase, wherein the first phase comprises a higher concentration of organic acid than the second phase, and wherein the second phase comprises the at least one azeotroping agent;

(iv) separating the first liquid stream into a first phase and a second phase, wherein the first phase comprises a higher concentration of organic acid than the second phase, and wherein the second phase comprises the at least one azeotroping agent; and (v) recovering the organic acid by separating the first phase from the second phase.

44. The process of claim 43, wherein recovered organic acid is heat stable.

45. The process of claim 43, wherein the recovered organic acid is an alpha hydroxy acid that is at least about 98% optically pure.

46. The process of claim 43, wherein the feed stream comprises at least one impurity, and wherein the at least one impurity is at a lower concentration in the organic acid recovered from the separated first phase than in the feed stream.

47. A process for obtaining an organic acid from a feed stream comprising at least one of an organic acid ammonium salt, an organic acid amide, or a alkylamine-organic acid complex, comprising the steps of:

mixing a feed stream and at least one azeotroping agent, wherein the feed stream comprises a fermentation broth wherein the fermentation broth comprises at least one of an organic acid ammonium salt, an organic acid amide, or a alkylamine-organic acid complex and wherein the organic acid of the salt, amide or complex is selected from the group consisting of monocarboxylic acids, dicarboxylic acids, and tricarboxylic acids having from 2 to 8 carbon atoms; and distilling the feed stream by a method comprising the steps of (i) heating at least one of the feed stream, the at least one azeotroping agent, or the mixture thereof, thereby (a) decomposing the ammonium salt, the amide, or the alkylamine-organic acid complex to produce organic acid, and (b) producing a first vapor stream that comprises at least one first azeotrope comprising the organic acid and the at least one azeotroping agent; and (ii) separating the first vapor stream from the mixture;

wherein the fermentation broth is at least partially purified prior to the mixing of the feed stream and the at least one azeotroping agent.

48. The process of claim 47, wherein the fermentation broth is purified using ion exchange prior to the mixing of the feed stream and the at least one azeotroping agent.

49. The process of claim 47, wherein the fermentation broth is acidified prior to the mixing of the feed stream and the at least one azeotroping agent.

50. A process for obtaining an organic acid from a feed stream comprising at least one of an organic acid ammonium salt, an organic acid amide, or a alkylamine-organic acid complex, comprising the steps of:

mixing a feed stream and at least one azeotroping agent, wherein the feed stream comprises an extract of a fermentation broth that comprises at least one of an organic acid ammonium salt, an organic acid amide, or a alkylamine-organic acid complex, and wherein the organic acid of the salt, amide or complex is selected from the group consisting of monocarboxylic acids, dicarboxylic acids, and tricarboxylic acids having from 2 to 8 carbon atoms; and distilling the feed stream by a method comprising the steps of (i) heating at least one of the feed stream, the at least one azeotroping agent, or the mixture thereof, thereby (a) decomposing the ammonium salt, the amide, or the alkylamine-organic acid complex to produce organic acid, and (b) producing a first vapor stream that comprises at least one first azeotrope comprising the organic acid and the at least one azeotroping agent; and (ii) separating the first vapor stream from the mixture.

51. The process of claim 50, wherein the fermentation broth is concentrated prior to preparing the extract from it.

52. The process of claim 50, wherein the fermentation broth is at least partially purified prior to preparing the extract from it.

53. The process of claim 52, wherein the fermentation broth is purified using ion exchange.

54. The process of claim 50, wherein the extract is prepared by extraction with a liquid extractant comprising alkylamine.

55. The process of claim 54, wherein the alkylamine is selected from the group consisting of trilaurylamine and tri-n-octylamine.

56. The process of claim 54, wherein the liquid extractant further comprises an extraction enhancer.

57. The process of claim 54, wherein the organic acid is lactic acid and the extraction enhancer is octyl-lactate.

58. The process of claim 54, wherein the liquid extractant further comprises a diluent.

* * * * *

UNITED STATES PATENT AND TRADEMARK OFFICE
CERTIFICATE OF CORRECTION

PATENT NO.   : 6,926,810 B2
DATED        : August 9, 2005
INVENTOR(S)  : Michael Charles Milner Cockrem and Istvan Kovacs It is certified that error appears in the above-identified patent and that said Letters Patent is hereby corrected as shown below:

Column 28,
Line 5, insert -- and -- after "atoms;".
Line 8, insert -- at least one -- before "azeotroping".
Line 9, delete "of" and insert -- thereof, --.
Line 11, insert a -- , -- after the second instance of "acid".
Lines 31, 33, 39 and 46, insert -- at least one -- after "the".
Line 35, insert -- further -- after "stream".
Line 52, insert -- the at least one -- after "comprises".

Column 29,
Line 13, insert -- at least one -- after "the".

Column 30,
Line 16, delete "a" and insert -- (a) --.

Column 31,
Line 23, insert a -- , --- after "broth".
Line 26, insert a -- , -- after "complex".

Signed and Sealed this

Fifteenth Day of November, 2005

JON W. DUDAS
*Director of the United States Patent and Trademark Office*